(12) United States Patent
Atanassov et al.

(10) Patent No.: US 8,642,308 B1
(45) Date of Patent: Feb. 4, 2014

(54) BIOFUEL CELL ELECTROCATALYSTS UTILIZING ENZYME-CARBON NANOTUBE ADDUCTS

(75) Inventors: Plamen Atanassov, Santa Fe, NM (US); Dmitri Ivnitski, Rego Park, NY (US); Ramaraja P. Ramasamy, Watkinsville, GA (US); Heather R. Luckarift, Port St Joe, FL (US); Glenn R. Johnson, Panama City, FL (US); Carolin Lau, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 287 days.

(21) Appl. No.: 13/178,420

(22) Filed: Jul. 7, 2011

Related U.S. Application Data

(60) Provisional application No. 61/399,093, filed on Jul. 7, 2010.

(51) Int. Cl.
*C12N 11/06* (2006.01)

(52) U.S. Cl.
USPC .................................................... 435/181

(58) Field of Classification Search
USPC .......................................................... 435/181
See application file for complete search history.

(56) References Cited

U.S. PATENT DOCUMENTS

2007/0077483 A1* 4/2007 Kubo et al. ..................... 429/43

OTHER PUBLICATIONS

Chen et al. "Noncovalent Sidewall Functionalization of Single-Walled Carbon Nanotubes for Protein Immobilization" J. Am. Chem. Soc. 2001, 123, 3838-3839.*

* cited by examiner

*Primary Examiner* — Thane Underdahl
(74) *Attorney, Agent, or Firm* — Gonzales Patent Services; Ellen M. Gonzales

(57) ABSTRACT

The present disclosure provides multi-walled carbon nanotubes and carbon nanotubes (CNTs) displaying catalytic enzymes bound to the nanotube sidewalls and devices, such as electrodes, incorporating these catalytic enzyme-bound CNTs (cebCNTs).

5 Claims, 23 Drawing Sheets

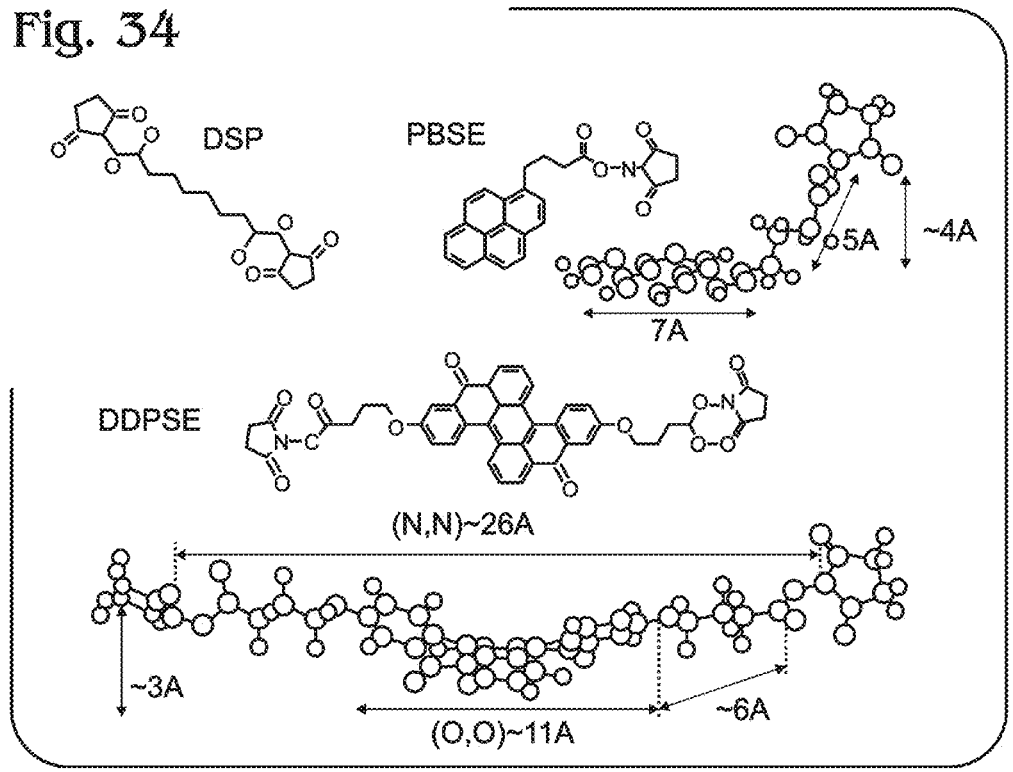
Fig. 34
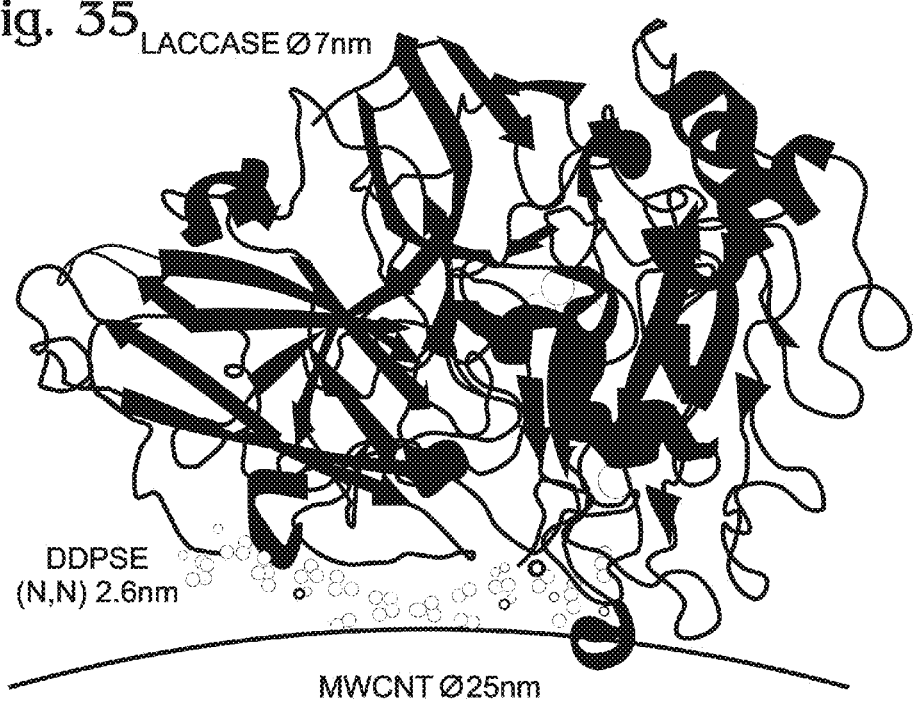
Fig. 35 LACCASE Ø7nm

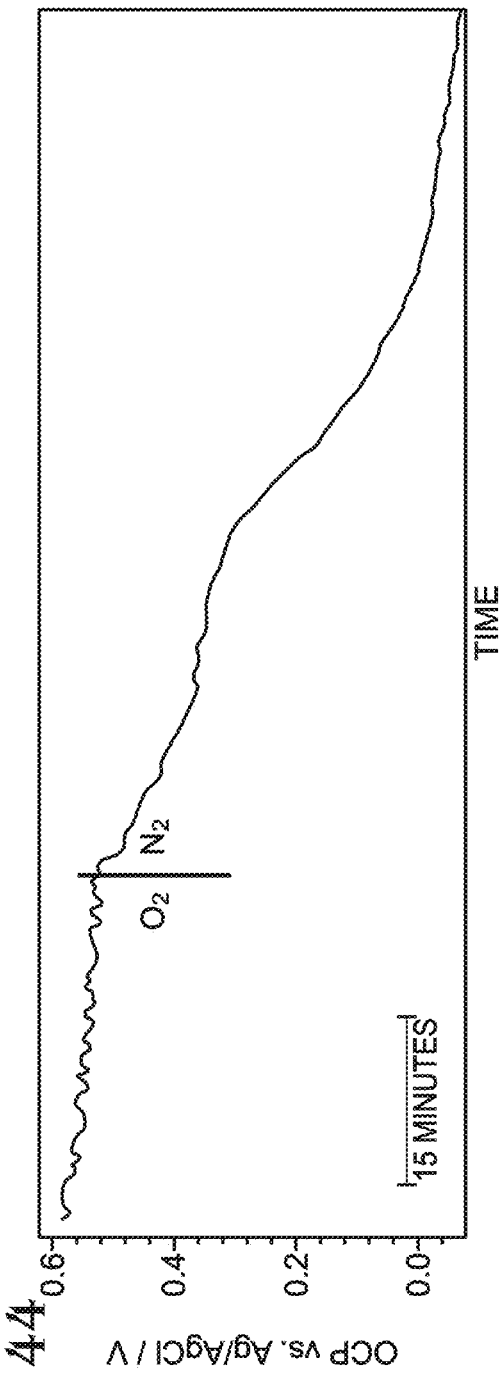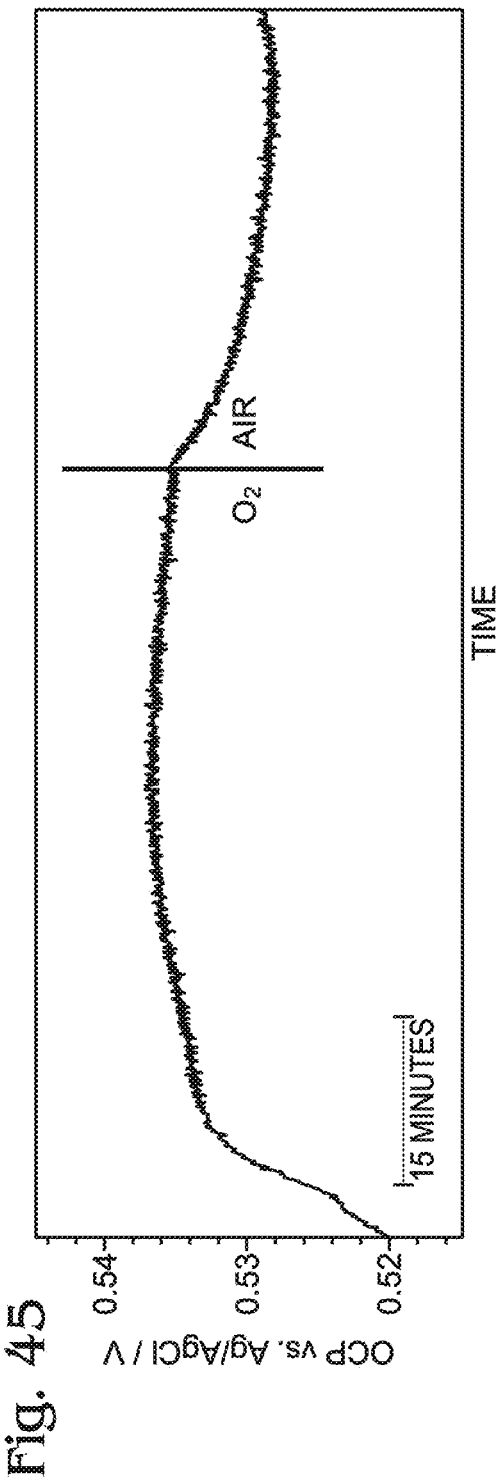

BIOFUEL CELL ELECTROCATALYSTS UTILIZING ENZYME-CARBON NANOTUBE ADDUCTS

CROSS-REFERENCE TO RELATED APPLICATIONS

The following application claims benefit of U.S. Provisional Application No. 61/399,093, filed Jul. 7, 2010, which is hereby incorporated by reference in its entirety.

STATEMENT REGARDING GOVERNMENT SPONSORED RESEARCH

This invention was made with Government support under grant MR 2D 100 awarded by AFO of Scientific Research & AFRL Materials Directorate and grant FA9550-06-1-0264 awarded by AFOSR MURI "Fundamentals and Bioengineering of Enzymatic Fuel Cells." The U.S. Government has certain rights in this invention.

SUMMARY

The present disclosure provides multi-walled carbon nanotubes and carbon nanotubes (CNTs) displaying catalytic enzymes bound to the nanotube sidewalls and devices, such as electrodes, incorporating these catalytic enzyme-bound CNTs (cebCNTs).

BACKGROUND

There is a great desire to find alternative methods of energy production. To this end, technologies like fuel cells, which rely on electro-oxidation of various catalysts are becoming increasingly popular. A growing area of interest is the area of biological fuel cells which use enzymatically oxidized biocatalysts for energy production.

Gas-diffusion electrodes (GDEs) have been widely used in alkaline and phosphoric acid fuel cells and in metal-air batteries where they are used to incorporate metal (Pt, Pd, Ag) or metal oxide ($MnO_2$, $Co_2O_3$) catalysts that are supported on dispersed carbonaceous materials (usually activated carbon or carbon blacks.) However, GDEs have been poorly explored for bio-catalytic systems, such as oxygen reduction catalyzed by multi-copper oxidases (MCO) due to the challenge of providing materials where the functional material: is electrically conductive with non-compromised electron conductivity; is hydrophilic enough to allow immobilization of the enzyme from an aqueous solution; has a functionalized surface (either naturally or is susceptible to synthetic functionalization strategies) to allow fortuitist enzyme-support interaction or chemical immobilization; and is susceptible to hydrophobization, either by chemical modification or by blending with a hydrophobic composite or dispersed phase (such as PTFE or PTFE-modified carbon black) to yield an effective transition to super-hydrophobicity, as required in the GDL.

Accordingly there is a need for novel biocathodes for biofuel cells that satisfy the above-identified conditions.

BRIEF DESCRIPTION OF THE DRAWINGS

FIG. 34 depicts the structure of the crosslinker DSP: (Dithiobis(succinimidyl)propionate); PBSE: 1-Pyrenebutyric acid N-hydroxysuccinimide ester and DDPSE: 4,4'-[(8,16-Dihydro-8,16-dioxodibenzo[a,j]perylene-2,10-diyl)dioxy]dibutyric acid di(N-succinimidyl ester).

FIG. 35 is a size comparison of laccase and DDPSE as crosslinker on a MWCNT having an approximately 25 nm diameter.

FIG. 44 is a graph showing monitoring the OCP of laccase adsorbed on a gas diffusion electrode under the influence of (A) oxygen and nitrogen stream.

FIG. 45 is a graph showing monitoring the OCP of laccase adsorbed on a gas diffusion electrode under the influence of ambient air.

DETAILED DESCRIPTION

According to various embodiments, the present disclosure provides functionalized carbon nanotubes or multi-walled carbon nanotubes (both of which are referred to herein inclusively as CNTs) covalently bound to biocatalysts via a linking agent, various electrodes incorporating the biocatalyst bound CNTs, methods for making the various electrodes, devices incorporating the electrodes, and methods for making those devices.

CNTs are known for their extraordinary electrical and mechanical properties, high surface area, low resistivity and chemical stability. This makes them an interesting material for various applications in microelectronics, composite materials and electrical applications. Conceptually, the CNTs walls consist of sp2 graphene carbon atoms with delocalized π-electrons which provide perfect tethering sites for other highly aromatic molecules. Conjugated polymers or aromatic carbon systems, like pyrenes or perylenes, for example, are known for their π-π stacking interaction with singe walled carbon nanotubes. Those non-covalent interactions are stronger than simple electrostatic binding or adsorption and as such provide an effective mechanism for associating biomolecules with CNT surfaces.

Figure 1:
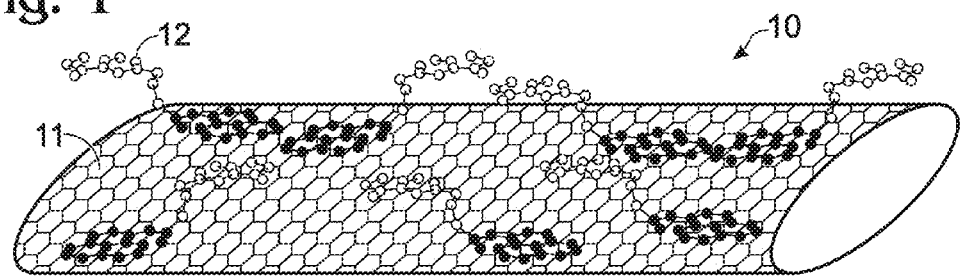
FIG. 1 is a schematic illustration of a carbon nanotube (CNT) functionalized with a linking agent.

Accordingly, in a first embodiment the present disclosure provides CNTs modified with bi-functional cross-linkers. As shown in FIG. 1, the sidewalls 11 of CNT 10 are modified so as to present a linking agent 12, the distal end of which is capable of binding with proteins or other biological species, thereby attaching the biological species to the CNT. A method for modifying CNTs using 1-pyrenebutanoic acid, succinimidyl ester (PBSE) is described in R. J. Chen et al., J. Amer. Chem. Soc. 2001, 123, 3838-3839, which is hereby incorporated by reference. Briefly, the aromatic pyrenyl moity interacts with the aromatic-like structure of the CNT walls through irreversible π-π stacking at the CNT and PBSE interface. Chen et al. demonstrated the attachment of proteins to CNTs using this process in order to produce highly specific electronic biosensors. See e.g., Chen et al. "Noncovalent functionalization of carbon nanotubes for highly specific electronic biosensors" PNAS 2003, vol. 100, no. 9, pp 4984-4989. It is important to note that unlike other techniques which only allow for modification of the CNT at the mouth of the tube, the method described herein allows for functionalization of the wall of the nanotube. According to various embodiments described herein, linkers other than PBSE may be used. For example, Dithiobis(succinimidyl)propionate (DSP) or 4,4'-[8,16-Dihydro-9,16-dioxodibenzo[a,j]perylene-2,10-diyl) dioxy]dibutyric acid di(N-succinimidyl ester) (DDPSE) may be used. Typically, the linkers will have a functionality consisting of a highly aromatic functional group (e.g. polycyclic aromatic hydrocarbons as well as heterocyclic macrocycles) which attaches through π-π-interactions to the CNT side walls and a protein binding group (e.g. amine group binding N-hydroxysuccinimide esters or imidoesters, sulfhydryl group binding maleimides or haloacetyles, carboxyl group binding carbodiimides, carbonyl group binding hydrazides as well as nonselective binding azides). Once functionalized with the linking agent, the CNT can then be incubated with proteins or other biological species so as to allow the amines on the surface of the biological species to form covalent amide bonds that link the biological species to the linking agent and therefore to the CNT.

According to another embodiment of the present disclosure, the functionalized CNTs are modified with enzymes known to catalyze oxygen reduction (i.e. redox enzymes), producing catalytic enzyme-bound CNTs (cebCNTs). Importantly, the mechanism for linking the enzyme to the CNT described herein retains the catalytic activity of the enzyme. Exemplary enzymes include, but are not limited to, multicopper oxidase (MCO) enzymes such as laccase, bilirubin oxidase (BOx) or ascorbate oxidase as well as other redox enzymes such as oxidases (e.g. glucose oxidase) or dehydrogenases (alcohol dehydrogenase, glucose dehydrogenase, malate dehydrogenase, aldose dehydrogenase).

Figure 2:
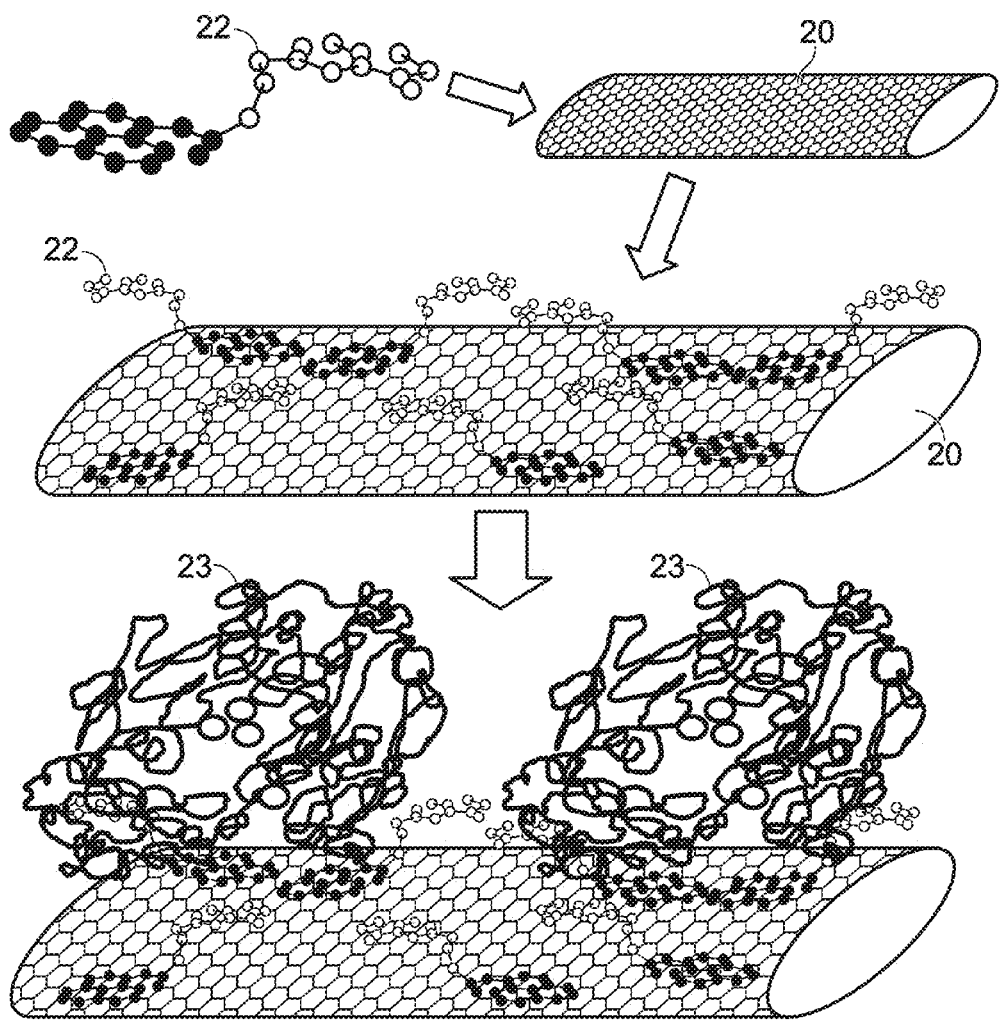
FIG. 2 is a schematic illustration of a process for immobilizing MCO enzymes onto a PBSE-modified CNT.

FIG. 2 provides a schematic illustration of the process for immobilizing MCO enzymes onto a PBSE-modified CNT. As shown, a CNT 20 is exposed under appropriate conditions to a linking agent 22, which is then bound to a redox protein 23, which may be, for example, an MCO enzyme such as laccase or BOx.

Figure 3:
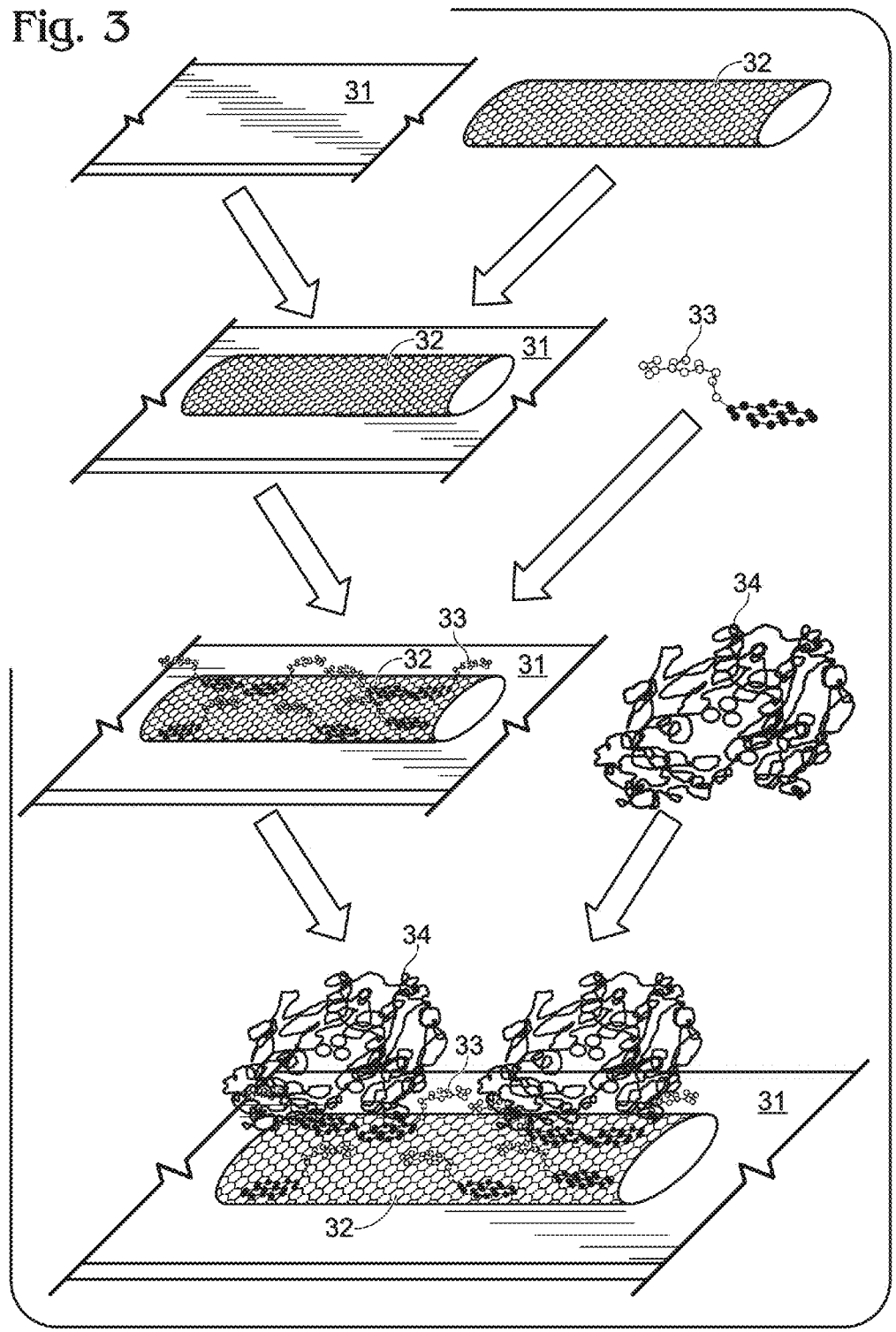
FIG. 3 is a schematic illustration of the process for producing an electrode incorporating enzyme-bound CNTs according to an embodiment of the present disclosure.

According to a further embodiment, the present disclosure provides an electrode including the catalytic enzyme-bound CNTs described above bound directly to the electrode. As shown in FIG. 3, an electrode 31 is first coated with CNTs 32, for example by heat fixing, and the resulting CNT-coated electrode is then modified, first by binding the linker agent 33 to the CNTs and then by binding the catalytic enzyme 34 to the linker agent. The result is an electrode which is able to undergo direct electron transfer between the enzyme redox center and the electrode itself. Exemplary electrodes include Toray® carbon paper (TP) electrodes (Toray Industries, Tokyo, Japan), Buckeye Paper® (Buckeye Technologies, Inc Memphis, Tenn.), multi-walled carbon nanotubes and rotating disc electrodes.

As a still further embodiment, the present disclosure provides a gas diffusion electrode. In general, a gas-diffusion electrode (GDE) comprises several layers of a carbon-polymer composite (including carbon black or graphite powder with PTFE or polyaniline as a binder) of varying hydrophobicity often integrated on a metallic mesh for mechanical stability and structural support. Three constituent layers are typically defined as backing material, a gas-diffusion layer (GDL) and a catalytic layer. The backing material serves as mechanical support and as an electron conductor. Calculations for enzymatic cathodes show a 5 to 10-fold increase in catalytic performance in respect to increased oxygen when supplied by gas phase diffusion rather than solute diffusion of dissolved oxygen. In-fact, an enzymatic rate dependence of laccase on the partial oxygen pressure has been show. An ideal GDL is completely hydrophobic (water repellant) and, in many cases, has an increasing hydrophilic character towards the electrolyte. The backing layer and GDL should both be highly gas-permeable, corrosion resistive, and highly electrically conductive. The catalytic layer contains the catalyst bound to a polymer-carbon mixture.

The balance of hydrophobic to hydrophilic properties determines the performance of the GDE. This balance is essential in providing the formation of an interfacial structure known as the "tri-phase interface" which is a line of contact of the gaseous, liquid, and solid phases responsible respectively for oxygen, hydronium oxide, and electron transport. Ideally, the GDE enables a high amount of surface area of the catalyst to be exposed to both the gas (air) and liquid (electrolyte) phases.

Figure 4:
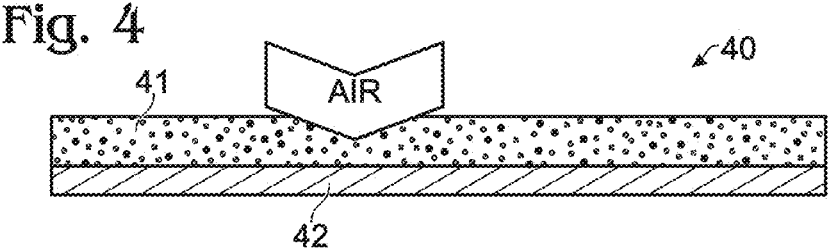
FIG. 4 is a schematic illustration of a gas diffusion electrode according to an embodiment of the present disclosure.

Accordingly, as shown in FIG. 4, one embodiment of a GDE 40 according to the present disclosure comprises a gas diffusion layer 41 formed from carbonized polytetrafluoroethylene (PFTE) and a catalytic layer 42 comprising enzyme-bound carbon nanotubes surrounding a binding agent such as PFTE.

Figure 5:
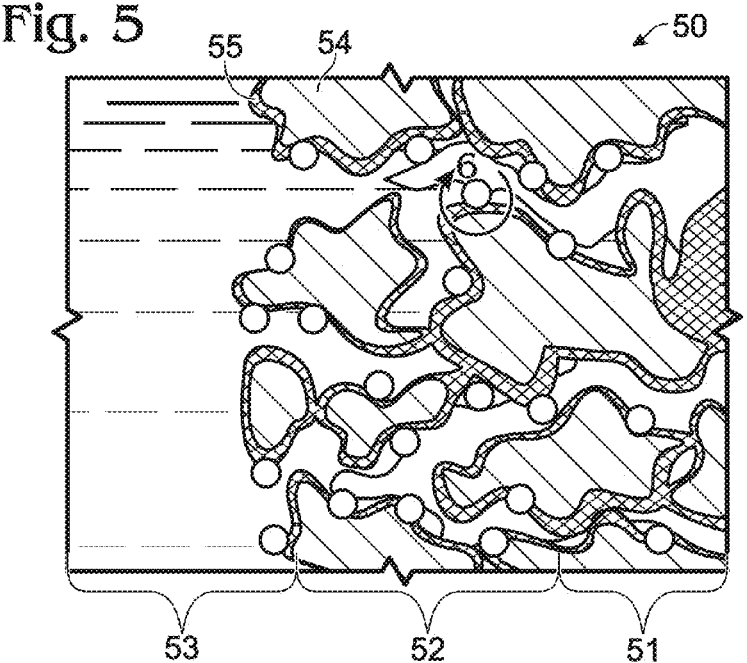
FIG. 5 is a close-up view of the various layers of a gas diffusion electrode according to an embodiment of the present disclosure.

A close up of the GDE is shown in FIG. 5, which shows electrode 50 including electrolyte layer 53, a catalytic layer 52, and a gas diffusion layer 51. The catalytic layer 52, is composed of composite 54 formed from the cebCNTs and a binding material. (As shown, the biocatalyst 55, is bound to the composite 54.) The binding material is typically a hydrophobic, oxygen permeable polymer such as PFTE, PANI (polyaniline type polymers). According to an embodiment, the CNT-binder composite may be formed by hot or cold hydraulic pressing into any desirable form and shape. The pressing also merges all layers (current collector, gas-diffusion and catalytic layer) together.

Figure 6:
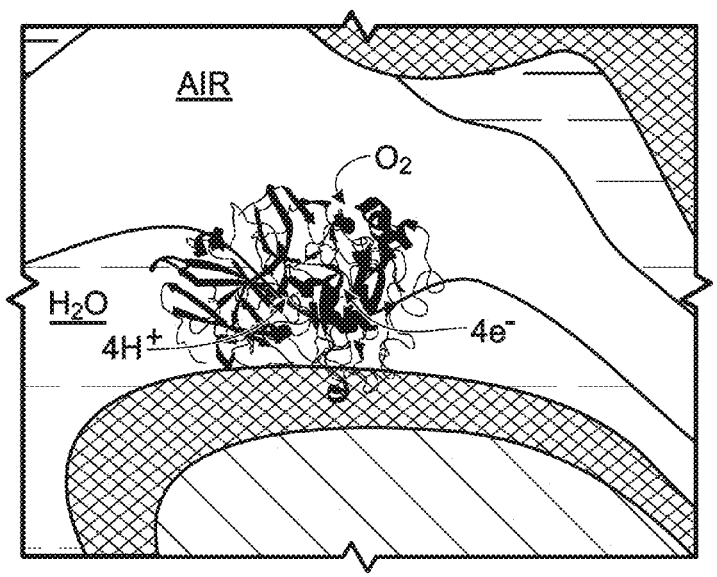
FIG. 6 is a still further close-up view of a gas diffusion electrode according to an embodiment of the present disclosure showing the three-phase contact zone.

Viewing FIG. 6, (a still further blow-up of a portion of FIG. 5) it can be seen that the resulting electrode enables the presentation of the enzymatic catalyst at the interphase of the electrolyte, electrode and air, thereby maximizing the opportunity for electron transfer between the electrolyte and the electrode.

Figure 7:
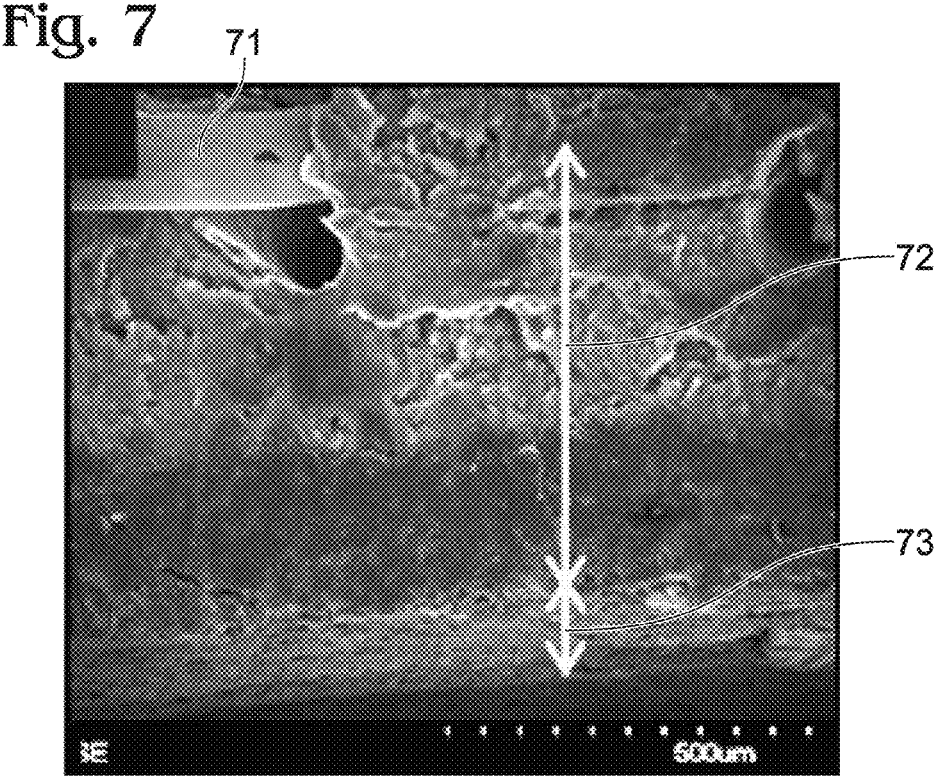
FIG. 7 is a cross sectional SEM image of an exemplary gas diffusion electrode according to an embodiment of the present disclosure.
Figure 8:
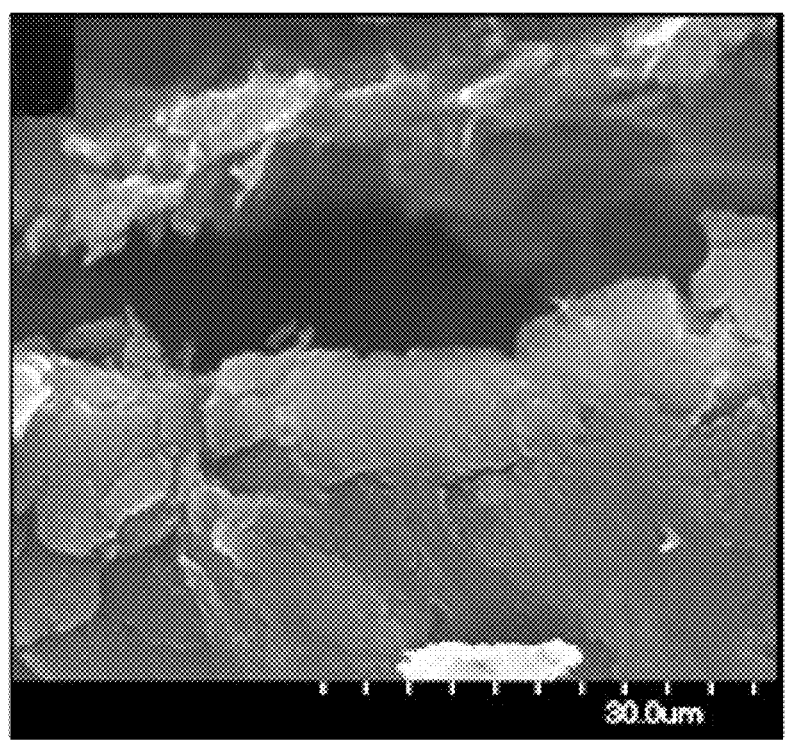
FIG. 8 is higher magnification SEM image of the carbon nanotube modified layer in a gas diffusion electrode of FIG. 7.

The limiting factor for catalytic as well as biocatalytic oxygen reductions is the transport of the gaseous reaction to the catalytic centers. Thus an efficient gas-diffusion electrode for enzymatic oxygen reduction reactions becomes extremely important for designing low-power biofuel cells. As discussed, an ideal gas-diffusion electrode is a layered design consisting of a gas-diffusion layer, a catalytic layer and if necessary a stabilizing (or binding) layer. Accordingly, one embodiment of the presently described gas-diffusion biocathode utilizes a carbon-PTFE composite material pressed onto a nickel mesh which provides mechanical stability, and additionally serves as current collector. A cross section SEM image (FIG. 7) of an exemplary electrode having this configuration shows the nickel wire 71 imbedded within the gas-diffusion layer 72 of about 500 μm total thickness and in direct contact with the catalytic layer 73 of ~100 μm thick. The layers may be fused together, for example, by hydraulic pressing. FIG. 8, a higher magnification SEM of the CNT catalytic layer, shows the typical sheet-like structure of the carbon nanotubes within the pressed composites.

The functionality and electrochemical performance of gas-diffusion electrodes is dictated by the hydrophobic and hydrophilic design properties of the gas diffusion and catalytic layers. As can be seen in FIGS. 5 and 6, the presently described gas-diffusion layer provides micro structured gas channels for an efficient oxygen supply in combination with electric conductivity, mechanical stability and water repellency. As host for the biocatalyst, the catalytic layer must provide hydrophilic micropores as well as hydrophobic gas diffusion pathways so that a three phase interphase can be formed. Biocatalysis takes place with its highest efficiency when this boundary of liquid electrolyte, gaseous substrate and solid catalyst on a carbon support is optimized. The transport of oxygen through the liquid phase is significantly hindered by diffusion and inherent low solubility in water. In the gas diffusion architecture shown in FIGS. 5-8, the three phase interphase is formed on the outside of the teflonized carbon or carbon nanotube particles. The aqueous electrolyte will primarily occupy larger pore spaces, whereas the gas transport is ensured by hydrophobic PTFE microchannels. The accumulation of electrolyte, known as a concept of "flooded pores", significantly hinders the oxygen transport and the electrode performance. Many models have been developed for the two-phase transport in porous gas-diffusion electrodes in order to optimize those systems. See e.g., S. Lister et al., Dev. Heat Transfer 2005, 19, 175. As a result, it is clear that a major design criteria for gas-diffusion electrodes are a well-balanced PTFE-to-carbon content and an optimal thickness of both layers. Common PTFE contents for gas diffusion layers are typically 25 wt % to 60 wt %. See e.g., F. Bidault et al., J. Power Sources 2009, 187, 39. Accordingly, it may be desirable to design the presently described gas diffusion layer to have a binder content of between 25 wt % and 60 wt %. According to one exemplary embodiment of the present disclosure, a gas-diffusion layer PTFE ratio of 35 wt % is selected to provide enough hydrophobic and water repellant character to seal the electrolyte yet provide an efficient gas supply by keeping the high electric conductivity of the carbon black materials. Reported thicknesses for metal catalyzed oxygen reduction reactions are approximately 500 µm for gas-diffusion layers and 150 µm for catalytic layers. Accordingly, it may be desirable to retain these design parameters.

Accordingly, the present disclosure provides multi-walled carbon nanotubes and carbon nanotubes (CNTs) displaying catalytic enzymes bound to the nanotube sidewalls and devices, such as electrodes, incorporating these catalytic enzyme-bound CNTs (cebCNTs). Further understanding of the various embodiments described herein will be gained from the Examples section below. However, it will be understood that the presently description is not limited to the Examples described herein and that the cebCNTs described herein can be used in a variety of other applications including, for example bioenergy devices such as biological fuel cells and particularly enzymatic fuel cells and hybrid microbial fuel cells with enzymatic cathode; and biosensing devices such as electrochemical galvanic sensors, or "self-powered" sensors, that are based on biological fuel cells, and particularly on enzymatic fuel cells or microbial fuel cells with enzymatic oxygen cathode, or hybrid or electrochemical oxygen sensors that operate under external polarization.

Accordingly, the specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "a nanotube" or "an enzyme" may include a plurality of nanotubes or a plurality of enzymes, respectively.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

I. V. Barsukov, C. S. Johnson, J. E. Doninger, V. Z. Barsukov, Vol. 229, Springer, Dordrecht, The Netherlands 2006.
F. Bidault, D. J. L. Brett, P. H. Middleton, N. P. Brandon, J. Power Sources 2009, 187, 39.
G. V. Shteinberg, A. V. Dribinsky, I. A. Kukushkina, M. Musilová, J. Mrha, J. Power Sources 1982, 8, 17.
D. A. Vaganov, N. G. Samoilenko, V. N. Bloshenko, V. G. Shteinberg, G. B. Manelis, Combust. Flame 2001, 126, 1803.
T. Berning, N. Djilali, J. Electrochem. Soc. 2003, 150, A1589.
S. Litster, N. Djilali, Dev. Heat Transfer 2005, 19, 175.
N. P. Brandon, D. J. Brett, Phil. Trans. R. Soc. A 2006, 364, 147.
E. I. Solomon, U. M. Sundaram, T. E. Machonkin, Chem. Rev. 1996, 96, 2563.
A. Messerschmidt, in Multi-copper oxidases, World Scientific, Singapore; River Edge, N.J. 1997.
P. Ramirez, N. Mano, R. Andreu, T. Ruzgas, A. Heller, L. Gorton, S. Shleev, Biochim. Biophys. Acta 2008, 1777, 1364.
O. Morozova, G. Shumakovich, M. Gorbacheva, S. Shleev, A. Yaropolov, Biochem. 2007, 72, 1136.
D. M. Ivnitski, C. Khripin, H. R. Luckarift, G. R. Johnson, P. Atanassov, Electrochim. Acta 2010, 55, 7385.
D. Ivnitski, P. Atanassov, Electroanal. 2007, 19, 2307.
A. Christenson, S. Shleev, N. Mano, A. Heller, L. Gorton, Biochim. Biophys. Acta 2006, 1757, 1634.
S. Shleev, A. Christenson, V. Serezhenkov, D. Burbaev, A. Yaropolov, L. Gorton, T. Ruzgas, Biochem. J. 2005, 385, 745.
I. Iliev, A. Kaisheva, F. Scheller, D. Pfeiffer, Electroanal. 1995, 7, 542.
S. Shleev, G. Shumakovich, O. Morozova, A. Yaropolov, Fuel Cells 2010, 10, 726.
M. R. Tarasevich, V. A. Bogdanovskaya, A. V. Kapustin, Electrochem. Comm. 2003, 5, 491.
R. Kontani, S. Tsujimura, K. Kano, Bioelectrochem. 2009, 76, 10.
G. Gupta, C. Lau, V. Rajendran, F. Colon, B. Branch, D. Ivnitski, P. Atanassov, Electrochem. Commun. 2011, 13, 247.
G. Gupta, C. Lau, B. Branch, V. Rajendran, D. Ivnitski, P. Atanassov, Electrochim. Acta 2011, In Press, Corrected Proof.
S. Iijima, Nature 1991, 354, 56.

M. in het Panhuis, A. Maiti, A. B. Dalton, A. van den Noort, J. N. Coleman, B. McCarthy, W. J. Blau, J. Phys. Chem. B 2002, 107, 478.

R. Chitta, A. S. D. Sandanayaka, A. L. Schumacher, L. D'Souza, Y. Araki, O. Ito, F. D'Souza, J. Phys. Chem. C 2007, 111, 6947.

R. P. Ramasamy, H. R. Luckarift, D. M. Ivnitski, P. B. Atanassov, G. R. Johnson, Chem. Comm. 2010, 46, 6045.

R. J. Chen, Y. Zhang, D. Wang, H. Dai, JACS 2001, 123, 3838.

T. J. Simmons, J. Bult, D. P. Hashim, R. J. Linhardt, P. M. Ajayan, ACS Nano 2009, 3, 865.

Z. Chen, A. Lohr, C. R. Saha-Moller, F. Wurthner, Chem. Soc. Rev. 2009, 38, 564.

C. Roquelet, J.-S. Lauret, V. Alain-Rizzo, C. Voisin, R. Fleurier, M. Delarue, D. Garrot, A. Loiseau, P. Roussignol, J. A. Delaire, E. Deleporte, ChemPhysChem, 11, 1585.

J. E. Klare, I. P. Murray, J. Goldberger, S. I. Stupp, Chem. Comm. 2009, 3705.

H. Jaegfeldt, T. Kuwana, G. Johansson, JACS 1983, 105, 1805.

H. Huang, W. Zhang, M. Li, Y. Gan, J. Chen, Y. Kuang, J. Colloid Interface Sci. 2005, 284, 593.

K. Tomantschger, K. V. Kordesch, J. Power Sources 1989, 25, 195.

J. Giner, C. Hunter, J. Electrochem. Soc. 1969, 116, 1124.

Y. Kiros, T. Quatrano, P. Bjornbom, Electrochem. Comm. 2004, 6, 526.

S. Calabrese Barton, Electrochim. Acta. 2005, 50, 2145.

A. M. Kuznetsov, V. A. Bogdanovskaya, M. R. Tarasevich, E. F. Gavrilova, FEBS Lett. 1987, 215, 219.

V. Svoboda, M. Cooney, B. Y. Liaw, S. Minteer, E. Piles, D. Lehnert, S. Calabrese Barton, R. Rincon, P. Atanassov, Electroanal. 2008, 20, 1099.

S. C. Barton, H.-H. Kim, G. Binyamin, Y. Zhang and A. Heller, J. Am. Chem. Soc., 2001, 123, 5802-5803; S. C. Barton, J. Gallaway and P. Atanassov, Chem. Rev., 2004, 104, 4867-4886; W. Zheng, H. Y. Zhao, H. M. Zhou, X. X. Xu, M. H. Ding and Y. F. Zheng, J. Solid State Electrochem., 2010, 14, 249-254.

E. I. Solomon, U. M. Sundaram and T. E. Machonkin, Chem. Rev., 1996, 96, 2563-2605; K. Piontek, M. Antorini and T. Choinowski, J. Biol. Chem., 2002, 277, 37663-37669.

S. Shleev, J. Tkac, A. Christenson, T. Ruzgas, A. I. Yaropopov, J. W. Whittaker and L. Gorton, Biosens. Bioelectron., 2005, 20, 2517-2554.

L. M. Ellerby, C. R. Nishida, F. Nishida, S. A. Yamanaka, B. Dunn, J. S. Valentine and J. I. Zink, Science, 1992, 255, 1113-1115; D. Ivnitski, K. Artyushkova, R. A. Rincon, P. Atanassov, H. R. Luckarift and G. R. Johnson, Small, 2008, 4, 357-364; M. Mazur, A. Krywko-Cendrowska, P. Krysinski and K. Rogalski, Syn. Metals, 2009, 159, 1731-1738; H. R. Luckarift, D. Ivnitski, R. Rincon, P. Atanassov and G. R. Johnson, Electroanal., 2010, 10.1002/elan.200980003.

J. M. Guisan, Immobilization of enzymes and cells, Humana Press, Totowa N.J., USA, 2006; P. F. Harris, Carbon Nanotube Science, Cambridge Publishers, Cambridge, UK, 2009.

R. J. Chen, Y. Zhang, D. Wang and H. Dai, J. Amer. Chem. Soc., 2001, 123, 3838-3839.

G. T. Hermanson, Bioconjugate Techniques, Elsevier Academic Press, New York N.Y., USA, 2008; K. Besteman, J.-O. Lee, F. G. M. Wiertz, H. A. Heering, and C. Dekker, Nano Lett., 2003, 3, 727-730.

E. Gileadi, Electrode Kinetics, VCH Publishers, New York, N.Y., USA, 1993.

W. Zheng, H. M. Zhou, Y. F. Zheng and N. Wang, Chem. Phys. Lett., 2008, 457, 381-385; M. Jonsson-Niedziolka, K. Szot, J. Rogalski and M. Apallo, Electrochem. Commun., 2009, 11, 1042-1044; K. Schubert, G. Goebel and F. Lisdat, Electrochim. Acta, 2009, 54, 3033-3038.

Ramasamy R P, Luckarift H R, Ivnitski D M, Atanassov P B, Johnson G R, Chemical Communications, 46 (2010), 5977-6188.

R. J. Chen, Y. Zhang, D. Wang and H. Dai, J. Am. Chem. Soc., 123 (2001), 3838-3839.

S. Lj. Gojkovic', S. Gupta, R. F. Savinell, Journal of Electroanalytical Chemistry, 462 (1999) 63-72.

N. M. Anastasijevic, Z. M. Dimitrijevic, R. R. Adzic, Electrochim. Acta, 31 (1986) 1125.

T. Jiang, G. M. Brisard, Electrochimica Acta, 52 (2007) 4487-4496.

S. Lj. Gojkovic', S. Gupta, R. F. Savinell, Electrochimica Acta, 45 (1999) 889-897.

EXAMPLES

Example I

MCO Immobilization onto PBSE-Modified Carbon Nanotubes on Toray® Carbon Paper Electrodes Experimental and Results Two MCO were selected as model redox enzymes, the laccase from *Trametes versicolor* and bilirubin oxidase (BOx) from *Myrothecium verrucaria*. The enzymes were immobilized on multi-walled CNT (MWCNT) by PBSE-modification of MWCNT directly on Toray® carbon paper (TP) electrodes. The tethered MCO-MWCNT conjugates were prepared as follows: 10 mm2 discs of Toray® carbon paper (TGP 090; Toray Industries, Tokyo, Japan) were used as the electrode base. For CNT modification of TP, 30 µL of MWCNT (1 mg·mL-1 in N,N-Dimethyl formamide) (Sigma, St. Louis, Mo.) was drop-cast onto TP and dried (50° C., 30 min). For sidewall functionalization of CNT with PBSE, the TP/MWCNT electrodes were soaked in a PBSE solution [1-Pyrenebutanoic acid succinimidyl ester; Anaspec Inc, Fremont, Calif.; (10 mM in N,N-DMF)] for 1 h at room temperature, washed thoroughly with N,N-DMF to remove excess PBSE and then with phosphate buffer (10 mM, pH 7). Laccase (Sigma) was dialyzed against CuSO4 (10 µM) in phosphate buffer (20 mM, pH 5.8) and then stored at −20° C. until use. Protein concentrations were determined using BCA assay (BCA Protein Assay Kit, Thermo Scientific Inc. Rockford, Ill.). BOx (Sigma) was used as received. For protein immobilization, PBSE-modified MWCNT/TP electrodes were incubated with 0.2 mL of laccase (0.5 mg·mL-1) or BOx (0.2 mg·mL-1) for 1 h in phosphate buffer (10 mM, pH 7.0). Excess protein was removed by washing with phosphate buffer and the electrode tested immediately in an electrochemical cell.

The enzyme immobilization efficiency was examined first using standard biochemical assays. The oxidase activity of laccase was determined in phosphate buffer (100 mM, pH 6.5) using syringaldazine (21.6 µM in CH3OH) (Sigma) by measuring the change in absorbance at 530 nm over time. One unit of activity was defined as 1 µmol of syringaldazine oxidized by laccase in 1 minute at 37° C. The catalytic activity of BOx was evaluated using bilirubin as substrate (0.002% in 0.2 M Tris HCl buffer, pH 8.4) by measuring the change in absorbance at 440 nm. One unit of activity was defined as 1 µmol of bilirubin oxidized by BOx in 1 minute at 37° C. The assay showed that ~20 U of laccase was associated with the electrode, corresponding to ~0.03 µg protein·mm-2 electrode. BOx activity proved to be too low to measure spectrophotometrically for the corresponding BOx-modified PBSE/MWCNT electrode. Since the activity measured in the standard assay does not represent electrochemical activity or oxygen reduction, further electrochemical characterization of the materials was done to determine whether an electronic connection was established for the protein, MWCNT, and TP composite material. The electrodes were held on a capped glassy carbon shaft electrode and tested in a 50 mL voltammetric cell (CH Instruments Inc, Austin, Tex.) with a glassy carbon counter electrode and a Ag/AgCl reference electrode (CH Instruments Inc.). Phosphate buffer (100 mM, pH 5.8, or pH 7.0 when noted) was used as the electrolyte throughout. CV scans were obtained by scanning from −0.2 V to 0.8 V at a sweep rate of 10 mV/s. Galvanostatic polarization measurements were obtained from 0 to 50 $\mu A \cdot cm-2$ at 10 $\mu A \cdot cm-2$ intervals and the voltage data points were recorded after 15 min at each step. Tafel slopes were obtained from the plots of working electrode potential versus kinetic current in the absence of convective transport.

Figure 9:
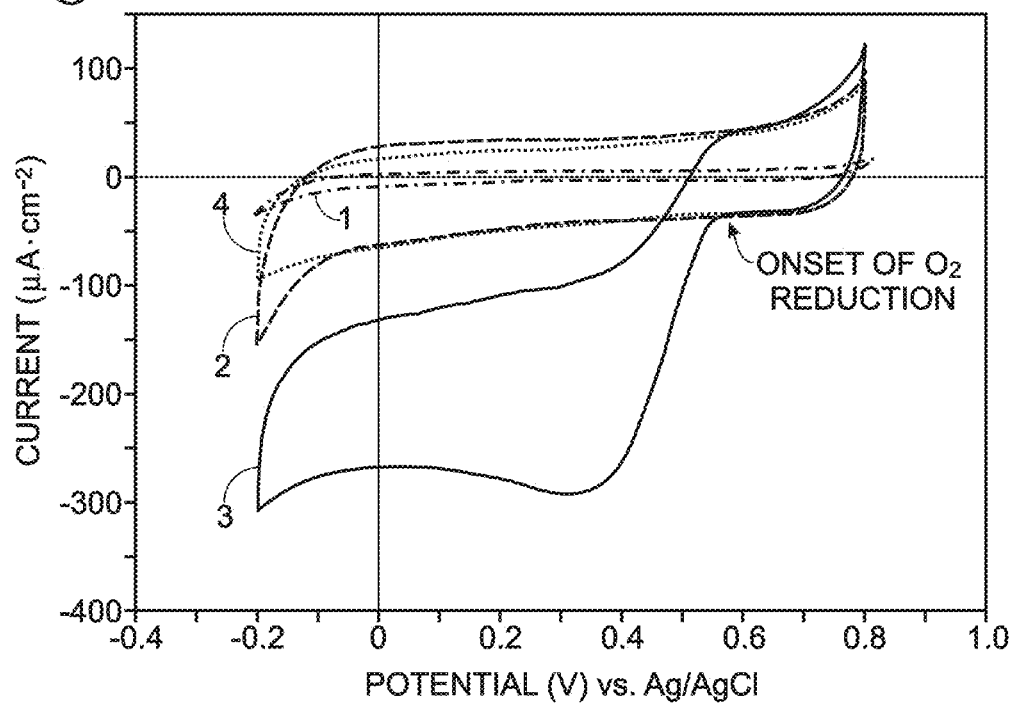
FIG. 9 is a Cyclic voltammogram (CV) of a model multi-copper oxidase (MCO) modified bioelectrodes (laccase as MCO). Key: (1) MCO physisorbed on bare TP, (2) MCO physisorbed on TP/MWCNT electrode; (3) MCO immobilized on PBSE-modified TP/MWCNT electrode; (4) electrode 3 in nitrogen-flushed electrolyte. CV scans in phosphate buffer electrolyte (pH 5.8), scan rate 10 $mV \cdot s^{-1}$, oxygen saturated electrolyte except as noted.

Cyclic voltammetry (CV) was used to evaluate the effectiveness of the PBSE-tether for functionalizing the TP/MWCNT-electrodes with enzyme. For control experiments, enzymes were associated directly to i) TP or ii) TP/MWCNT through noncovalent physisorption. Laccase adsorbed directly on TP showed no evidence of electrocatalytic activity for oxygen reduction (FIG. 9). Despite a theoretically short electron tunneling distance between the enzyme redox center and the electrode, the open circuit potential (OCP) for the oxygen reduction reaction was 0.44±0.03 V; n=4, significantly lower than the thermodynamic maximum (0.688 V vs. Ag/AgCl). TP modified with MWCNT had higher capacitance (increased electrochemical surface area) but marginally increased OCP (0.49±0.02 V; n=3). Although the nanomaterial dimensions may bring about close physical binding between laccase and MWCNT that could facilitate electron tunnelling, there was no evidence for interfacial DET or electrocatalytic activity.

Figure 10:
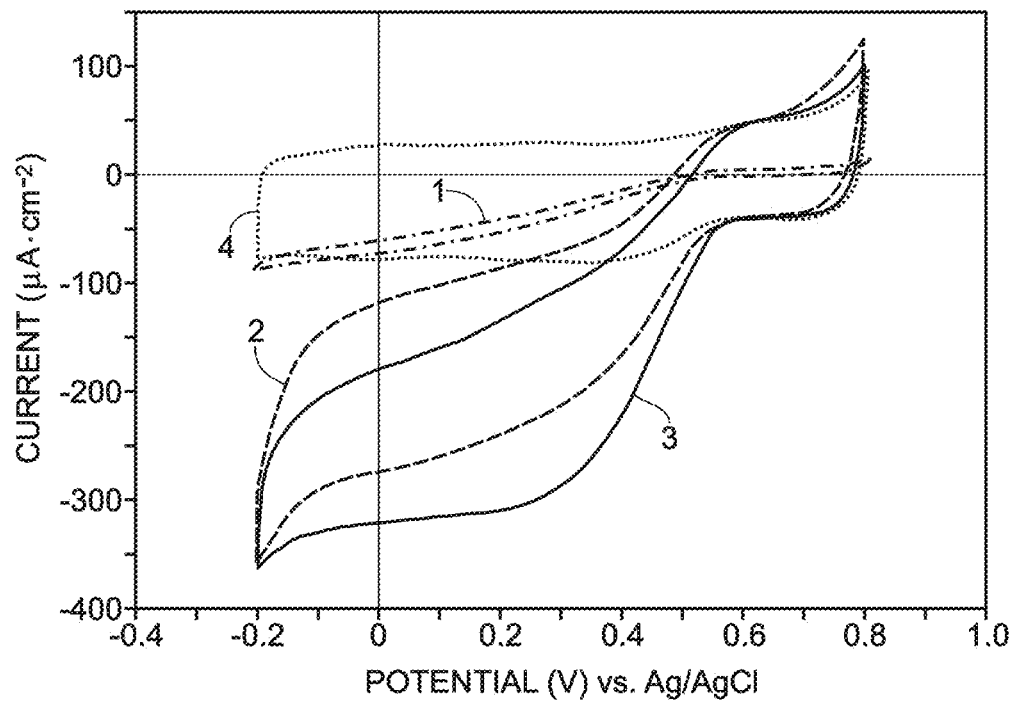
FIG. 10 is a Cyclic voltammogram (CV) of a model multi-copper oxidase (MCO) modified bioelectrodes (bilirubin oxidase as MCO). Key: (1) MCO physisorbed on bare TP, (2) MCO physisorbed on TP/MWCNT electrode; (3) MCO immobilized on PBSE-modified TP/MWCNT electrode; (4) electrode 3 in nitrogen-flushed electrolyte. CV scans in phosphate buffer electrolyte (pH 5.8), scan rate 10 $mV \cdot s^{-1}$, oxygen saturated electrolyte except as noted.

When laccase was tethered to MWCNT via PBSE, the CV results depicted obvious electrocatalytic activity for oxygen reduction. The cathodic sweep showed a dramatic deflection from the control electrode processes below 0.6 V. The OCP, onset and half-peak potentials were 0.60±0.01 V, 0.60±0.01 V, and 0.47±0.02 V; n=3, respectively and diffusion limitation conditions were reached at ~0.4 V during the cathodic sweep. The voltammetric response of the PBSE-tethered laccase provided a Tafel slope of 18 mV/decade in the kinetic region above 0.57 V and a slope of 24 mV/decade from 0.5 to 0.55 V. The Tafel slopes approach the theoretical limit (15 mV) for a four-electron-transfer reaction, and compare favorably with slopes for conventional oxygen reduction catalysts.8 The CV trace for nitrogen-sparged electrolyte shows no catalytic current with the tethered laccase, confirming that the deflection seen in the cathodic sweep corresponds to oxygen reduction (FIGS. 9-10).

The methodology was examined further using BOx as an oxygen reduction catalyst. The PBSE-tethered BOx electrode (FIG. 10) also showed high electrocatalytic activity (OCP: 0.62±0.005 V; n=3), the onset and half-peak potentials for the electrodes were 0.61±0.02 V and 0.45±0.03 V, respectively. The OCP at neutral pH was ~0.56 V, about 75 mV higher than that reported in the literature for a covalently linked BOx on MWCNT.9 The CV traces of oxygen- and nitrogen-sparged electrolyte show a clear distinction between catalytic and capacitive processes, indicating a high electrocatalytic activity of BOx. Unlike laccase, BOx exhibited apparent electrocatalytic activity after simple physisorption onto the TP or TP/MWCNT electrodes without the PBSE tether. The response may result from undefined surface characteristics of BOx that bring about preferential orientation of the enzyme T1 copper site compared to laccase, or simply a higher specific catalytic activity for the commercial BOx preparation.

Figure 11:
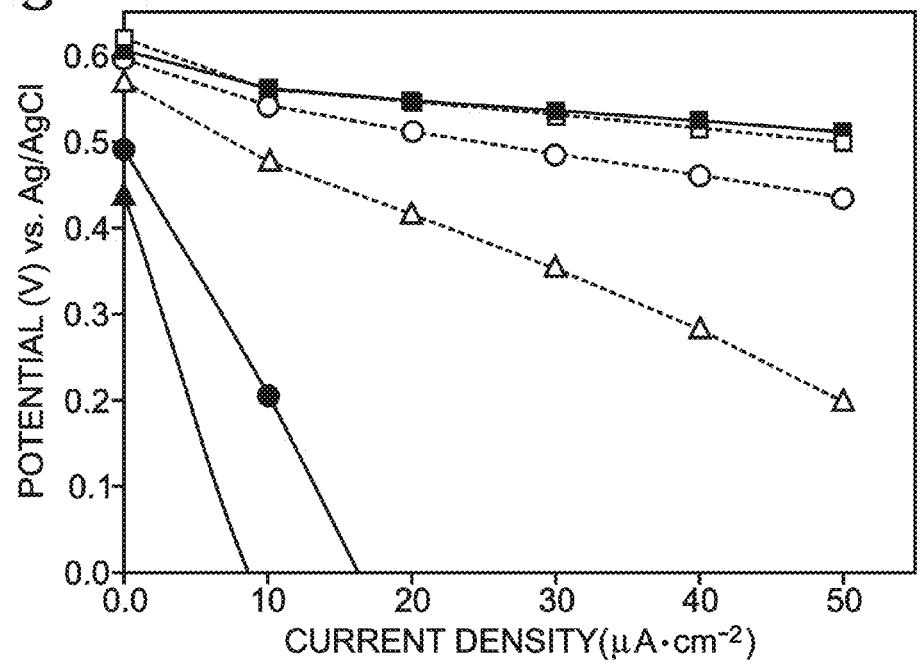
FIG. 11 shows the Galvanostatic polarization curves for laccase (solid lines, closed symbols) and BOx (dotted lines, open symbols) electrodes. Key: (triangles) MCO physisorbed on bare TP; (circles) MCO physisorbed on TP/MWCNT electrode; (squares) MCO immobilized on PBSE-modified TP/MWCNT electrode. Note: Potentials <0 are not shown; the plotted curves extrapolate beyond the x-axis and are based on all measured data.

Galvanostatic measurements at steady state revealed that the tethered MCO exhibit exceptionally stable performance with potential losses of less than 100 mV at 50 $\mu A \cdot cm-2$, relative to the OCP. By comparison, laccase physisorbed onto TP or TP/MWCNT-modified could not sustain high faradic currents (FIG. 11). The BOx on TP and TP/MWCNT electrodes, however, showed comparably better performance than laccase controls, in agreement with the CV results.

The PBSE-modified TP/MWCNT electrodes supported faster and more complete bioelectrochemical oxygen reduction than the physisorbed control materials and facilitated DET for immobilized MCO at current densities much greater than previous reports.9 The galvanostatic measurements for the MCO confirm the fabrication of a stable, conductive, bioelectrocatalytic interface between the enzyme and electrode that may be attributed to a variety of factors. The PBSE-modification of MWCNT via π-π stacking preserves the electronic properties of the MWCNT to allow efficient electron transport through the matrix. The covalent link between a MCO and the PBSE-tether will position the enzyme close to the MWCNT and reduce the electron tunneling distance between the enzyme and the electrode. In addition, the distribution of amines on the protein surface will guide orientation with the MWCNT. The limited electrochemical activity measured for control electrodes (no PBSE) is attributed to a small fraction of MCO molecules that align favorably during physisorption on TP or MWCNT. The response is evident from the higher OCP measured with MWCNT on TP (0.49 V) when compared to that of protein-free MWCNT (0.09 V). The high OCP, however, did not translate to electrocatalytic activity, possibly due to unfavorable orientation of the majority of catalyst molecules on the MWCNT surface or poor catalyst loading. A detailed understanding of the biophysical interactions at the interface that lead to efficient bioelectrocatalysis will require additional characterization and modeling.

Conclusions

The bio-conjugates formed using PBSE effectively link MCO with MWCNT to facilitate DET and bioelectrocatalytic oxygen reduction. The catalytic efficiency was significantly greater than previous reports for MCO electrodes. The process provides a porous, potentially scalable, architecture that can advance bioelectrocatalytic applications. Future research will provide a deeper understanding of the attachment mechanism that directs enzyme orientation and provide guidance to optimize the interaction further. The applicability to alternative catalysts was demonstrated with two MCOs but could be extended to a wider range of biomolecules and applications.

Example II

MCO Immobilization onto PBSE-Modified Carbon Nanotubes on Rotating Disc Electrodes Experimental and Results A glass electrochemical cell of 125 ml capacity was used to carry out all the experiments. The electrolyte used was 100 ml of 100 mM potassium phosphate buffer (pH 5.8). The electrolyte was prepared using monobasic and dibasic potassium phosphates (BDH chemicals). Distilled, deionized water at 18 MΩ conductivity was used to prepare all the solutions. Silver/silver chloride electrode (CH Instruments) was used as the reference electrode and platinum wire (CH Instruments) was used as the counter electrode. A glassy carbon disc-platinum ring electrode (from Pine Instruments) was used as the working electrode. A potentiostat (CH Instruments) was used to control both the disc and ring potentials. The rotation rate was controlled by the Pine instruments setup. CH Instruments software interface was used to control the potentiostat and also record the data. The glassy carbon disc was polished with 0.3 μm pore size Alumina powder and then washed thoroughly with water. The clean disc electrode was inserted into the rotating ring disc assembly. The disc electrode was first coated with multiwalled carbon nanotubes by heat fixing at about 70° C. and then incubated with the hetero-bifunctional cross linking agent 1-Pyrenebutanoic acid succinimidyl ester (PBSE) obtained from Anaspec Inc. The excess cross linker was washed away using N,N-dimethyl formamide and phosphate buffer (pH 7). After washing, the enzyme laccase (Sigma Life sciences) from Tramates versicolor was immobilized on this surface by incubation for about 30 minutes. The electrolyte was initially saturated with pure oxygen (99.9% purity) and then experiments were carried out on the rotating ring-disc electrode. Linear sweep voltammograms were obtained for the ring and the disc at different rotation rates and at 1 V constant ring potential. This value of 1 V was selected after comparing the voltammograms at different ring potentials. The disc potential was swept from 0 to 0.8 V. Also, Tafel plots were obtained for the disc at various rotation speeds by sweeping the potential from 0.33 V to 0.73 V. Various kinetic parameters such as Tafel slopes, half peak potentials, number of electrons and rate constants were obtained from the recorded voltammogram and Tafel plot data.

Standardization of the Experimental Conditions

Figure 12:
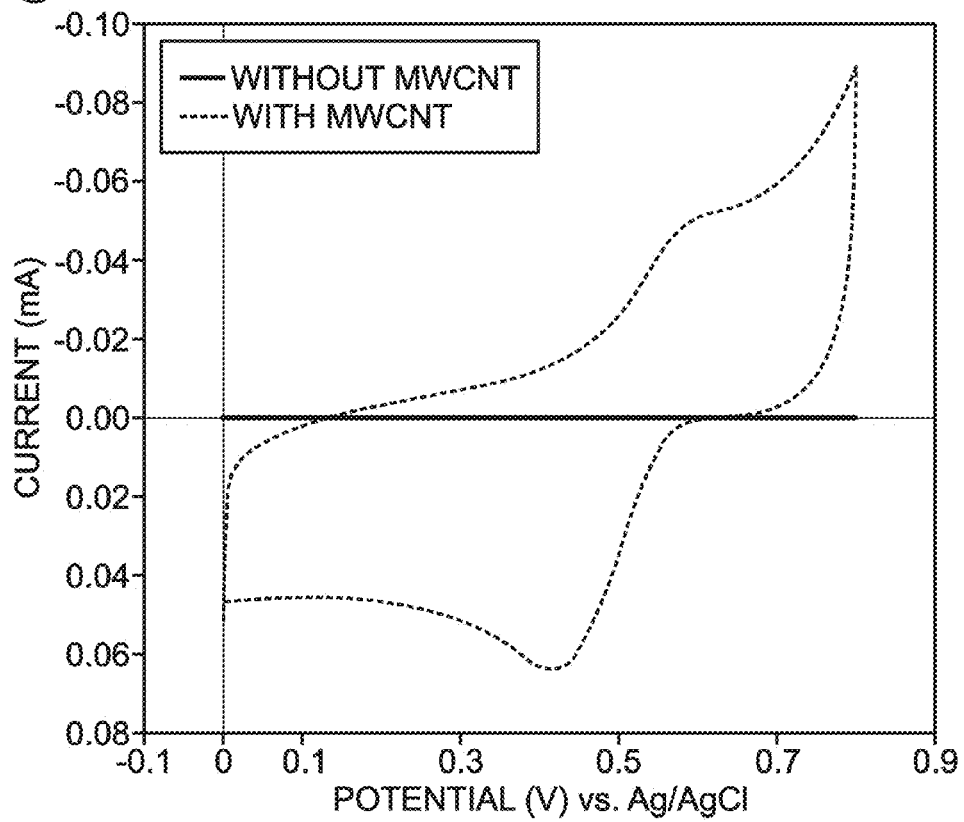
FIG. 12 is a cyclic voltammogram obtained in oxygen-saturated electrolyte comparing the presence and absence of nanotubes.
Figure 13:
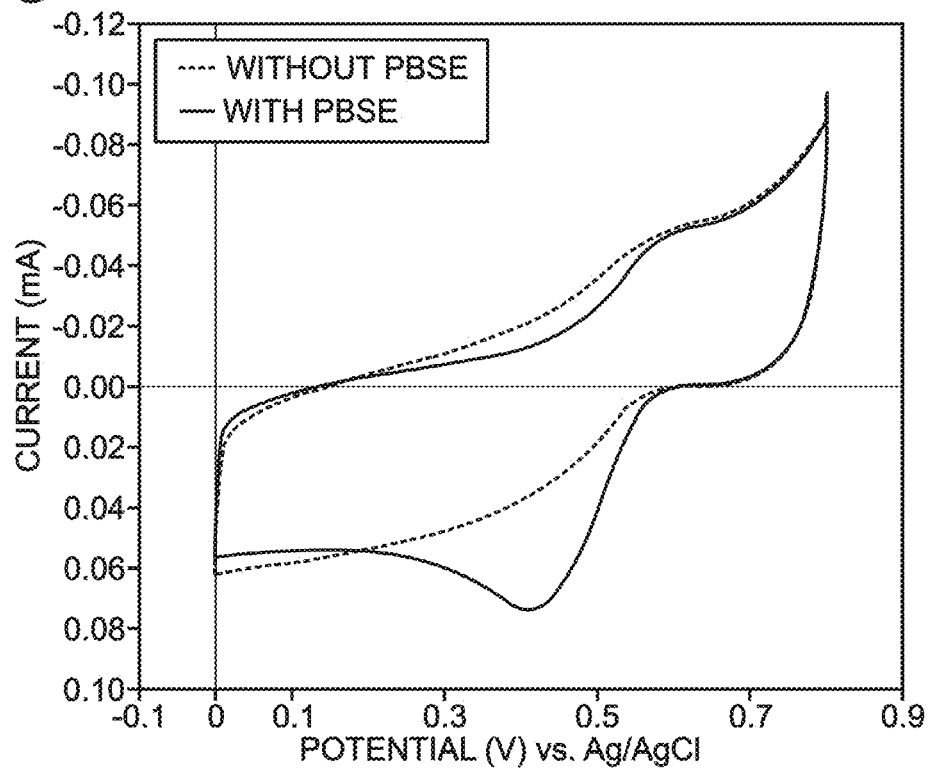
FIG. 13 is a cyclic voltammogram obtained in oxygen-saturated electrolyte comparing the presence and absence of PBSE.
Figure 14:
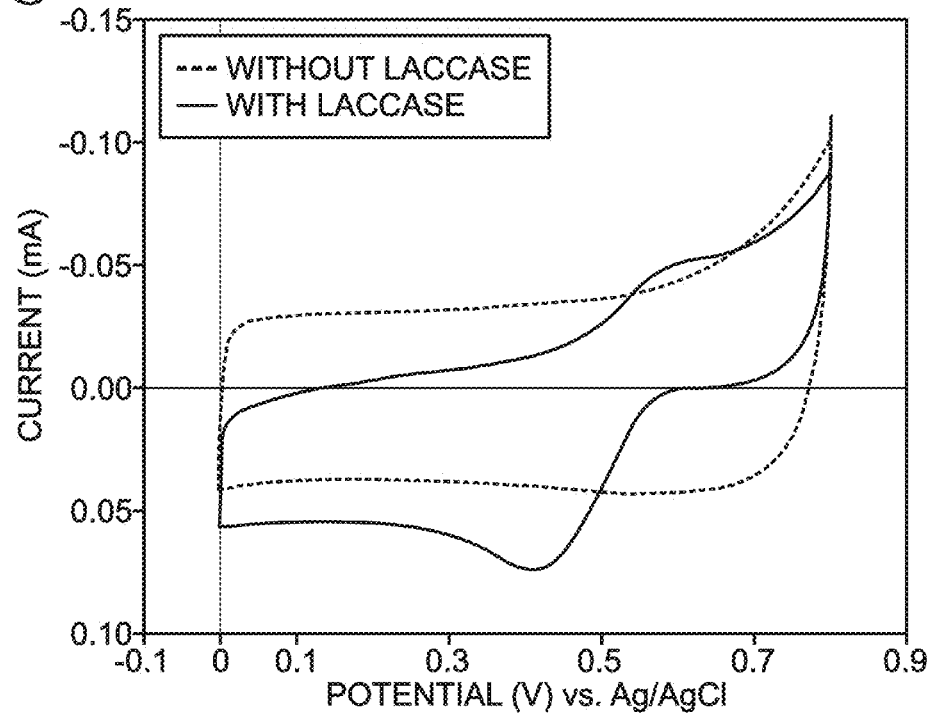
FIG. 14 is a cyclic voltammogram obtained in oxygen-saturated electrolyte comparing the presence and absence of Laccase.
Figure 15:
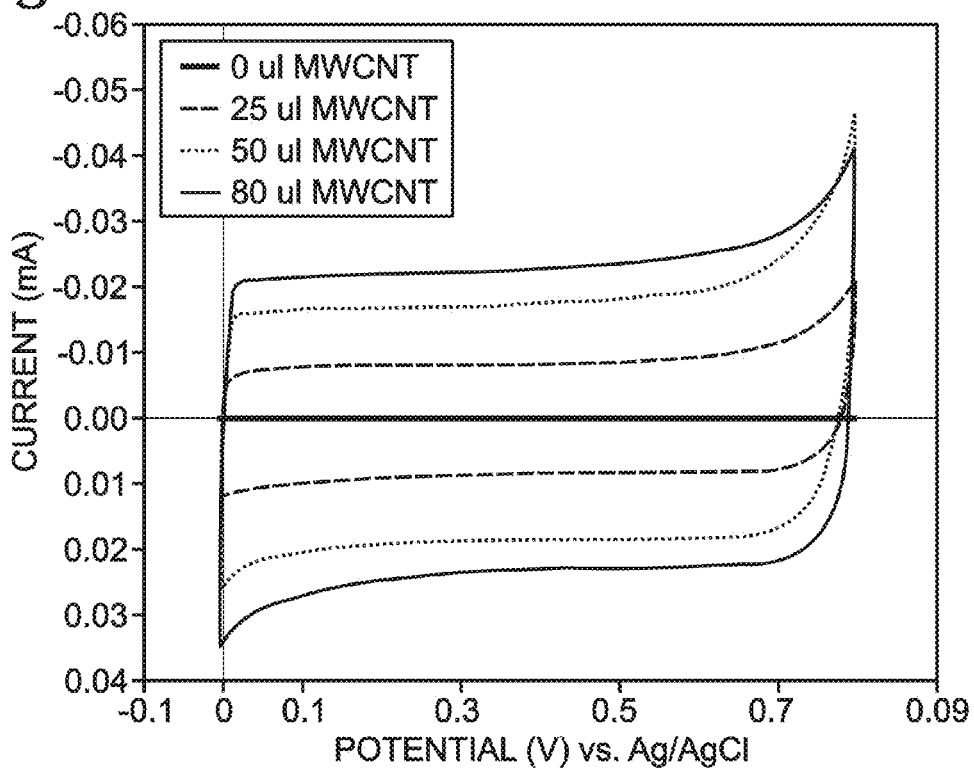
FIG. 15 is a comparison of the cyclic voltammograms obtained in nitrogen-saturated electrolyte for different multi-walled carbon nanotube loadings showing the variation in capacitance.

The catalytic ability of the nanobiocomposite was reiterated by studying the effect of the absence of each of its individual components on the oxygen reduction. FIGS. 12-14 show the cyclic voltammograms in oxygen saturated electrolyte for the three different cases of absence of carbon nanotubes, PBSE or Laccase. The voltammograms of the composite in all the three cases showed better oxygen reduction than in the absence of any individual component. This was in complete agreement with the data reported previously using Toray paper electrode. Multi-walled carbon nanotubes provide a large electrochemical surface area for enzyme immobilization on the electrode. Therefore, as the amount of nanotubes increased, the electrochemical surface area increased and hence, better oxygen reduction was observed. However, it has been found that when the amount of carbon nanotubes increased beyond 0.16 mg, the cyclic voltammogram showed decrease in oxygen reduction probably be due to a thick coating on the electrode resulting in hindered oxygen diffusion.

Figure 16:
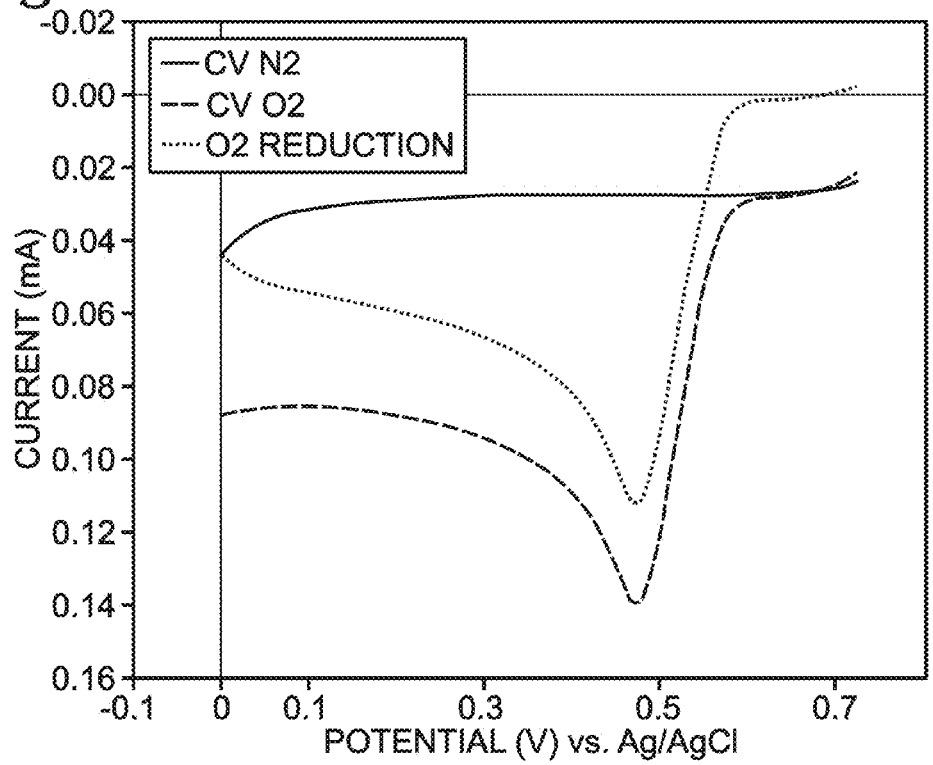
FIG. 16 is a voltammogram of the electrode coated with Laccase-nanobiocomposite using the standardized concentrations of each individual component, recorded in nitrogen and oxygen saturated electrolyte, and the actual oxygen reduction curve obtained by subtracting the nitrogen CV from the oxygen one.

1-pyrenebutanoic acid succinimidyl ester has been previously reported for its use in functionalizing carbon nanotubes. The pyrene rings of the hetero-bifunctional cross linker interact with the carbon nanotubes and the NHS-ester group interacts with the amino group of the enzyme, thereby establishing an effective electrical communication between the enzyme and the carbon nanotubes. The concentration of this cross-linker should be ideal for establishing a good connection between the nanotubes and the enzyme but should not be too high to form a polymer film, which increases the resistance to electron flow. The best set of concentrations for each of the individual components of the bionanocomposite was qualitatively determined from the cyclic voltammograms at different concentrations. FIG. 16, shows the voltammograms of the enzyme nanocomposite coated electrode in deoxygenated (nitrogen saturated) electrolyte and in oxygen saturated electrolyte. The actual oxygen reduction voltammogram is obtained by subtracting the nitrogen voltammogram from the oxygen one.

Rotating Ring-Disc Electrode Analysis

Figure 17:
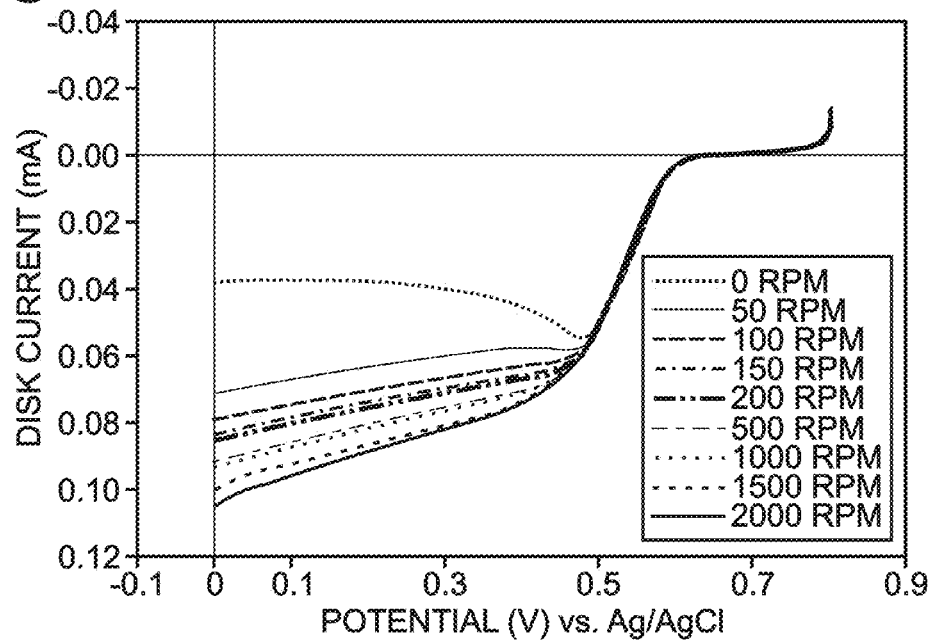
FIG. 17 is a linear sweep voltammograms at various rotation speeds, sweep rate 10 mV/s.
Figure 18:
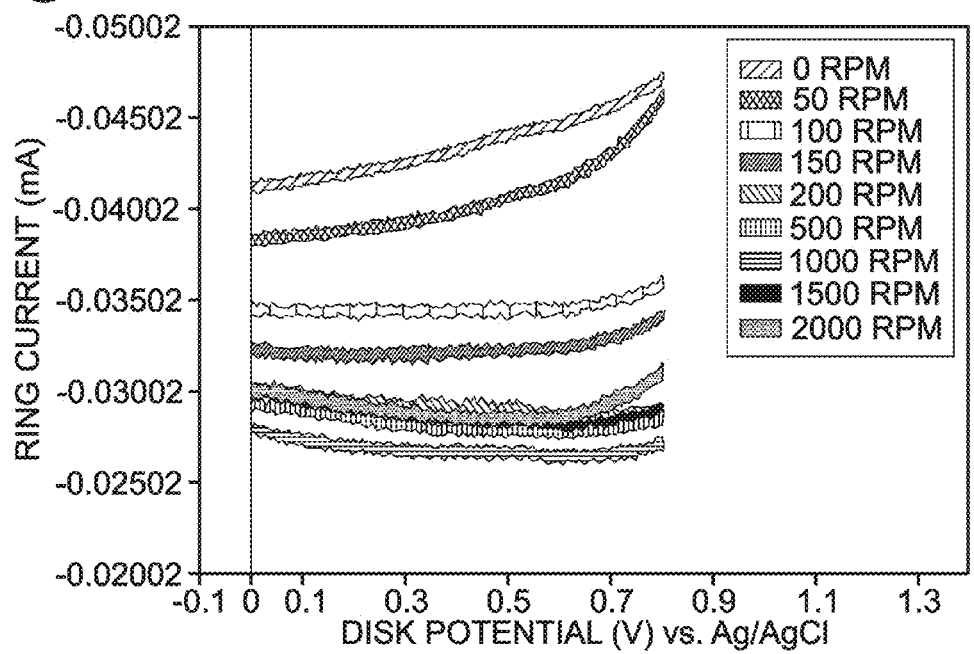
FIG. 18 is a plot of ring current versus disc potentials at various rotation speeds of the rotating-ring disc electrode.

The glassy carbon disc of the rotating ring-disc electrode was coated with the nanobiocomposite described previously and inserted into the platinum ring-disc assembly. The open circuit potential measured was found to be 0.632 V. This was higher than the values obtained for all the electrodes prepared previously, indicating that the catalyst is very effective for oxygen reduction. Cathodic linear sweep voltammograms for both the ring and the disc of the rotating ring-disc electrode coated with the nanobiocomposite were obtained at different rotation rates as shown in FIGS. 17 and 18. The disc potential was swept from 0 to 0.8 V while the ring potential was held at 1 V. When the electrode was not rotated, the voltammogram showed a steep fall and then a rise again, indicating an oxygen diffusion limitation at the electrode surface. Due to insufficient oxygen availability, the reduction current reduces. This mass transfer limitation was overcome by rotating the electrode. Hence, except at 0 RPM, no limiting current plateau was observed for any rotation speed. The disc currents showed a clear increase in the limiting current with increase in the rotation speed although the oxygen reduction slope was similar. At higher rotation speeds, more oxygen can diffuse to the electrode surface and is available to the catalyst for reduction, hence more the limiting current.

The ring currents were lower in the kinetic and diffusion limitation region compared to the region above the open circuit potential. This conforms to our expectation that at high disc potentials more peroxide intermediate is formed since the catalyst cannot initiate the 4-electron oxygen reduction whereas at lower disc potentials 4-electron reduction is predominant. The ring currents also showed a decrease in magnitude with increase in rotation speed, but at extremely high speeds the trend reversed. This could probably mean that at extremely high rotation speeds, there is not enough time for the peroxide intermediate to get oxidized back to oxygen at the ring surface before diffusing into the bulk (electrolyte).

Order of the Reaction

Figure 19:
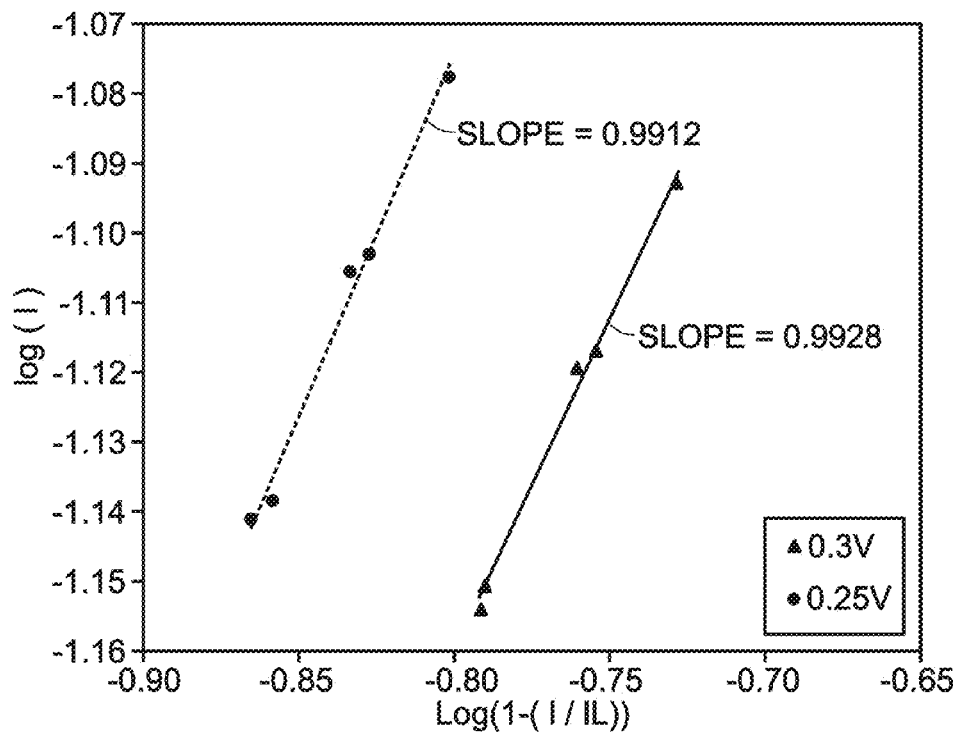
FIG. 19 shows the order of the reaction plot at disc potentials of 0.25 V and 0.3.

The order of the overall oxygen reduction reaction is determined by the relationship between the measured current values and the limiting currents for different rotation rates in the Levich region. The plots are expected to be linear in the kinetic region (disc potential below open circuit potential) according to the following equation:

$$\log I = \log I_{kin} + p\log\left(1 - \frac{I}{I_L}\right)$$

where I is the measured current, IL is the limiting current. Current value at 0 V disc potential was chosen as the limiting current. The kinetic current is obtained from the intercept and the reaction order is the slope. FIG. 19 shows the order of the reaction plot at disc potentials of 0.25 V and 0.3 V which are well within the oxygen reduction region. The slope of these straight lines is nearly one, therefore the oxygen reduction kinetics is first order for our system.

Rotation Speed Effect

Figure 20:
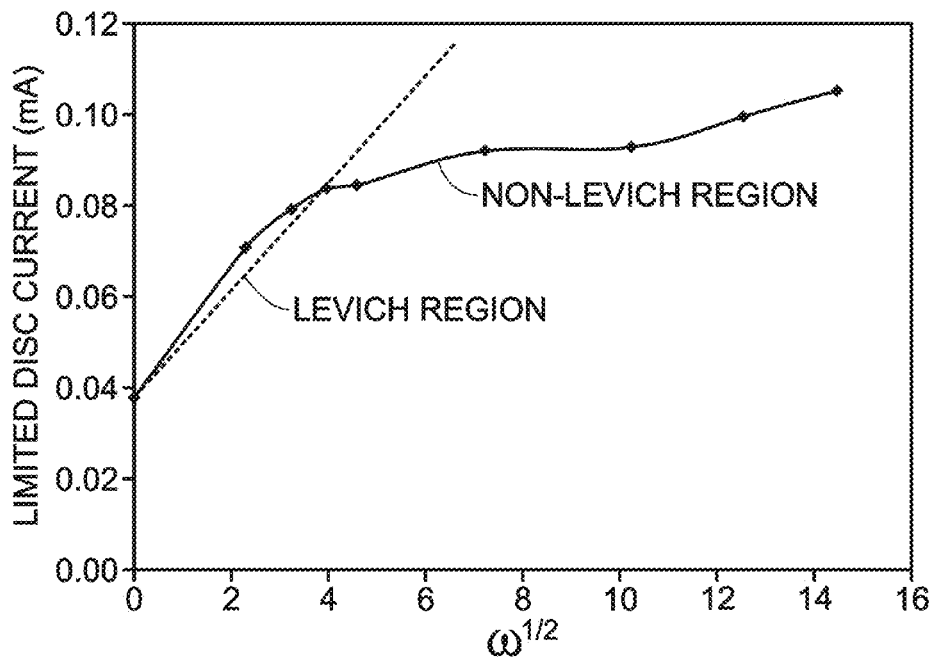
FIG. 20 is a plot showing the Levich and Non-Levich regions for the Laccase-nanobiocomposite-RRDE system.

A graph of limiting current versus square root of rotation speed was plotted in order to determine the rotation rate limit beyond which there is no free diffusion of oxygen to the electrode surface. The linear region is the rotation speeds up to which the Levich kinetics applies and number of transferred electrons can be calculated. In the non-linear region, there is high turbulence and the rotation speeds are too high to enable oxygen to diffuse to the electrode surface and undergo reduction. The Levich and Non-Levich regions for our catalytic system are shown in FIG. 20.

Koutecky-Levich Plot:

The Koutecky-Levich equation for a first order reaction is given by:

$$\frac{1}{I} = \frac{1}{I_{kin}} + \frac{1}{B\omega^{\frac{1}{2}}}$$

where $\omega$ is the rotation speed and B is the Levich slope given by:

$$B = 0.62nFScD^{\frac{2}{3}}v^{-\frac{1}{6}}$$

where n is the number of electrons transferred per oxygen molecule, F is the Faraday's constant, S is the electrode surface area, c is the oxygen bulk concentration in the electrolyte, D is the diffusion coefficient for oxygen in the electrolyte and v is the kinematic viscosity of the electrolyte.

Figure 21:
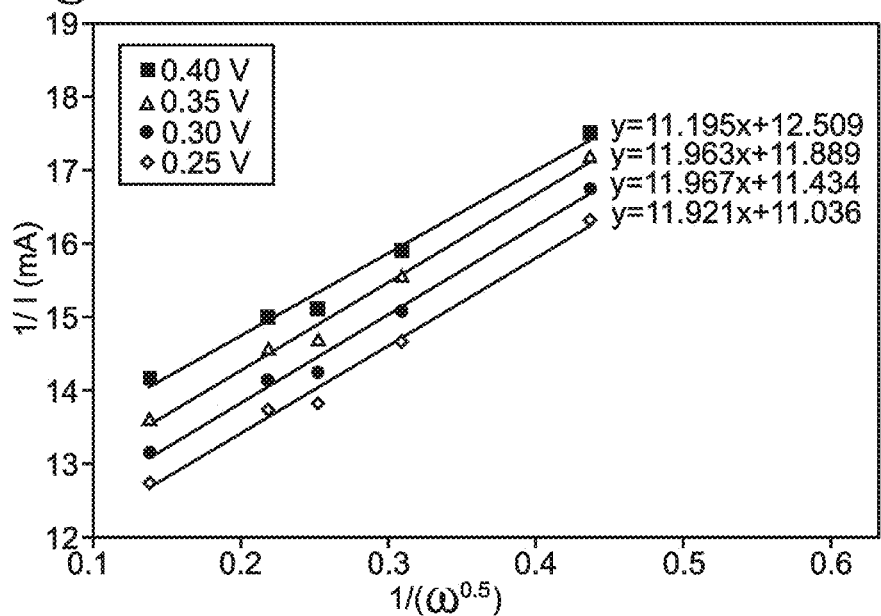
FIG. 21 is a Koutecky-Levich plot at various disc potentials in the kinetic region. The slope and intercept are obtained from the straight line equations.

FIG. 21 shows the Koutecky-Levich plots different rotation speeds in the kinetic region. The slope of the lines at different disc potentials was nearly the same and its average value was 11.76. The parallel lines obtained affirm that the number of electrons transferred per molecule of oxygen is independent of the disc potential. For our catalytic system the average number of electrons transferred was calculated from the slope 1/B. Faraday's constant is 96485. The diameter of the disc was specified as 0.5 mm (Pine Instruments specification sheet). Using data from literature, the solubility of oxygen, c was taken as 1.26×10−3 mol/L, the diffusion coefficient of oxygen (D=2.6×10−5 cm2/s), the kinematic viscosity (v=0.9×10−2 cm2/s). The number of electrons transferred per molecule of oxygen was calculated to be between 3.6 and 4 at high rotation speeds.

Tafel Slope

Figure 22:
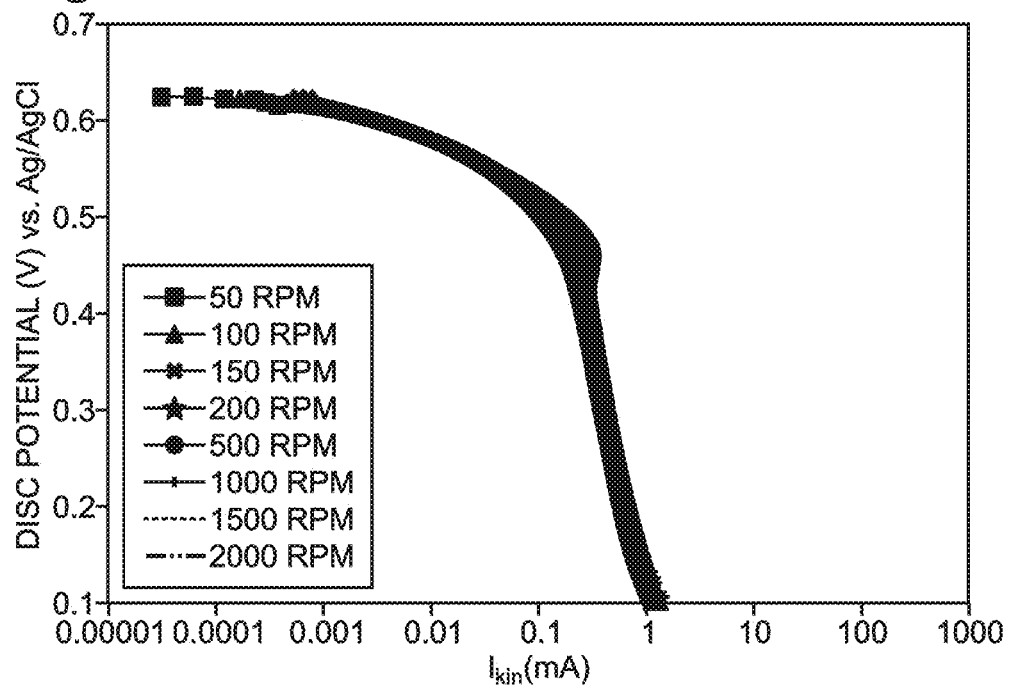
FIG. 22 shows Tafel plots obtained from the kinetic current data at different rotation speeds.

The oxygen reduction ability of the catalyst can be quantified by the Tafel plot. A graph of disc potential versus Ikin is plotted as shown in FIG. 22. The slope of the linear region is the Tafel slope. The theoretical value of this parameter for a four electron reduction is 15 mV/decade change of current. Therefore, the closer the experimental value is to this value, the lesser is the intermediate formation and hence, the better the catalyst. The obtained Tafel slope for our catalyst is 23 mV/decade changes. This value increases to 31 at very high rotation speeds indicating lesser extent for 4 electron reaction. These values are much better than the Tafel slopes obtained with other catalysts for oxygen reduction.

Number of Electrons

Figure 23:
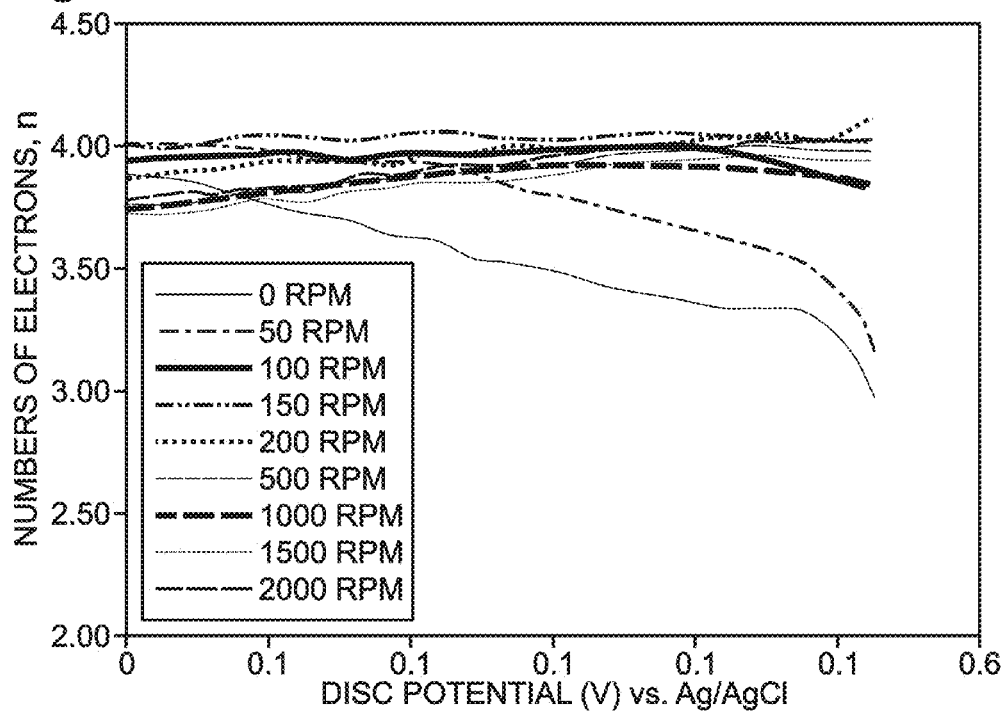
FIG. 23 shows the number of electrons as a function of disc potential at different rotation speeds in the oxygen reduction (kinetic) region.

The average number of electrons transferred per molecule of oxygen calculated from mass and charge balances for two electron and four electron transfer is given by the following equation:

$$n = \frac{4}{1 + \frac{I_R}{NI_D}}$$

where n is the number of electrons, IR is the ring current, ID is the disc current and N is the collection efficiency. The collection efficiency of RRDE is 0.256. (PINE Instruments data sheets). The number of electrons transferred is calculated using the above equation and a graph of n versus disc potential was plotted as shown in FIG. 23. At lower rotation speeds (Levich region), the number of electrons transferred is nearly four and decreases slightly as the disc potentials approaches the open circuit potential. Only in the no rotation case, the decrease is significant and the number of electrons transferred falls from nearly 4 to 3 in the kinetic region.

Tafel Curve and Electron Transfer Rate Constant

Tafel equation is used to study the dependence of the electron transfer kinetics on the electrode potential. It is written as:

$$I = a + b\exp\eta$$

where a and b are constants and $\eta$ is the overpotential.

Figure 24:
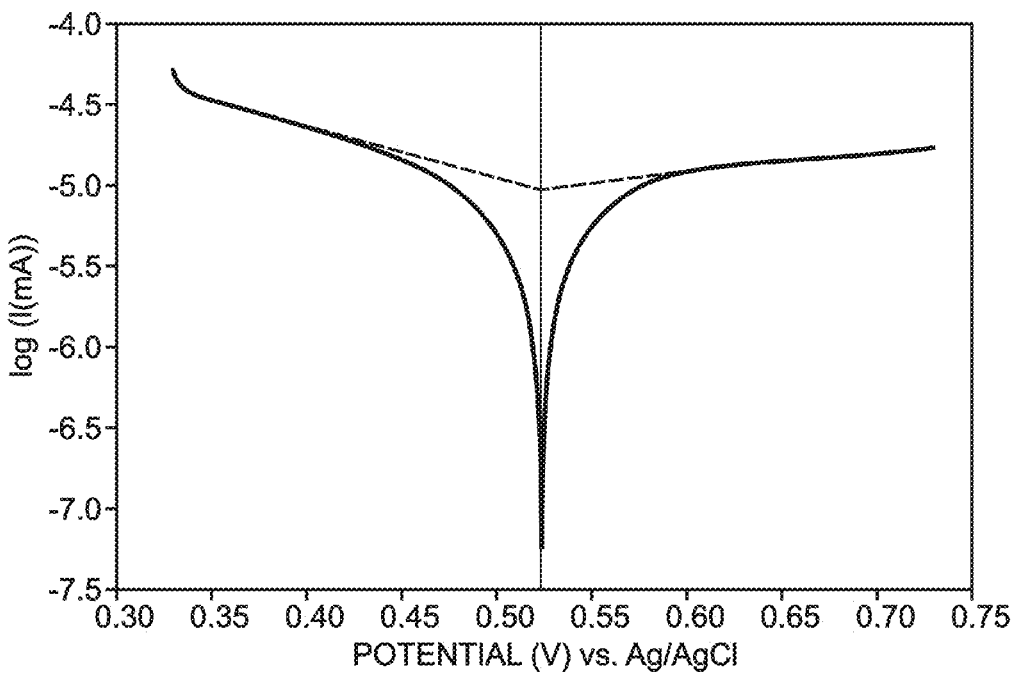
FIG. 24 is a Tafel curve at 0 RPM.
Figure 25:
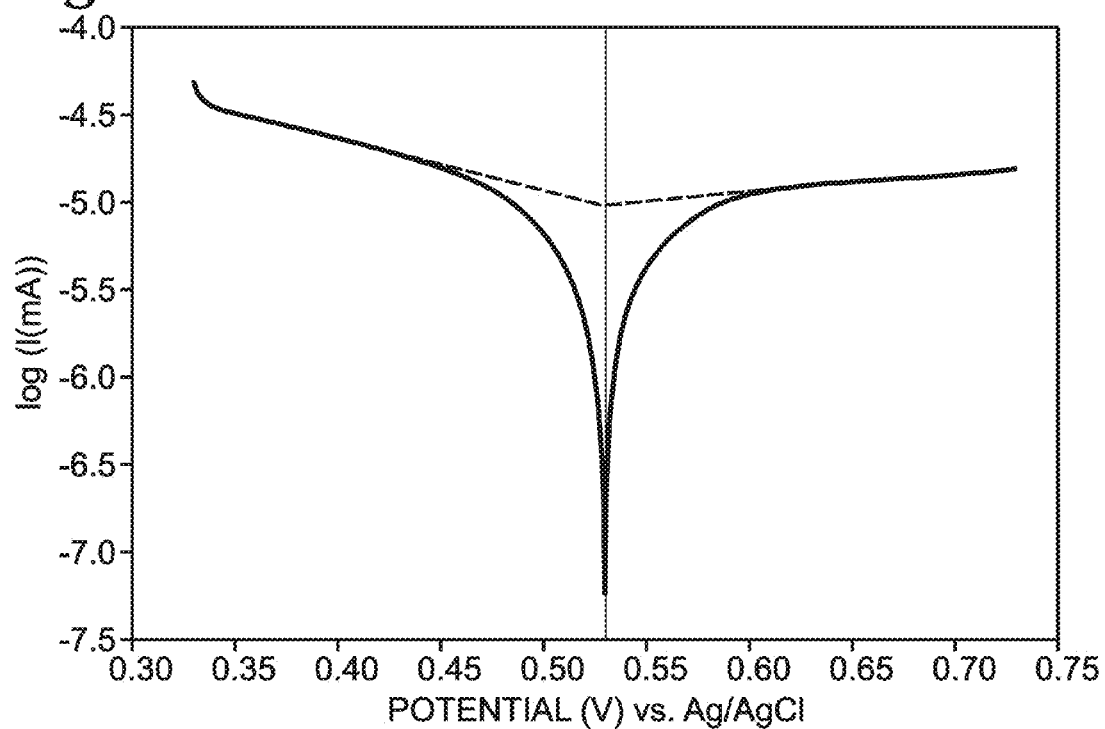
FIG. 25 is a Tafel curve at 100 RPM.
Figure 26:
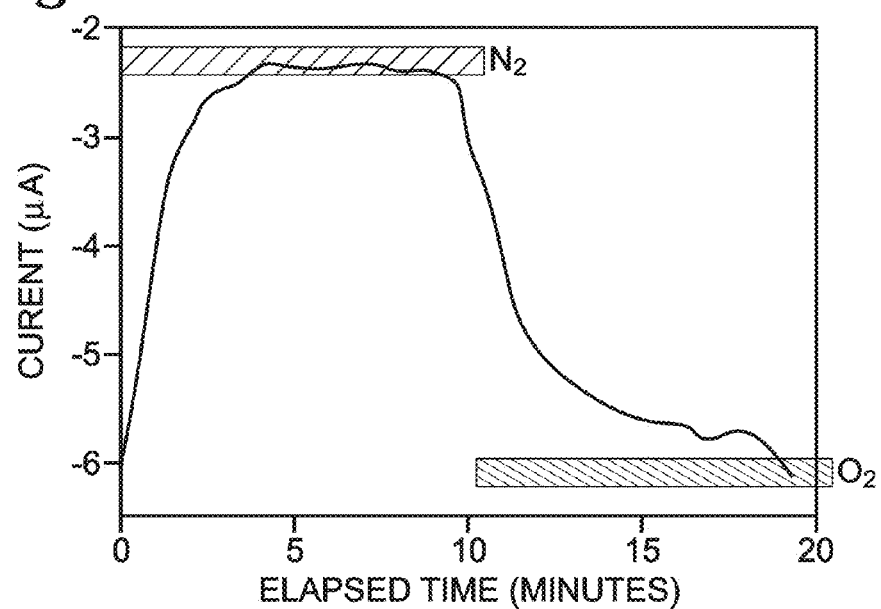
FIG. 26 is a graph showing current generation of an MCO catalyst immobilized to buckypaper via PBSE over a 20 minute time period.
Figure 27:
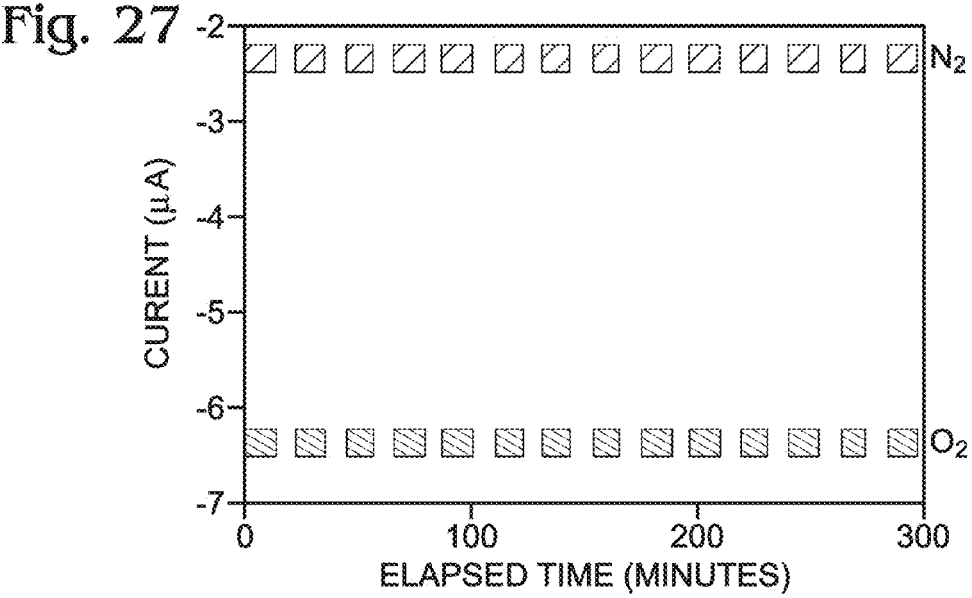
FIG. 27 is a graph showing current generation of an MCO catalyst immobilized to buckypaper via PBSE over a 300 minute time period.
Figure 28:
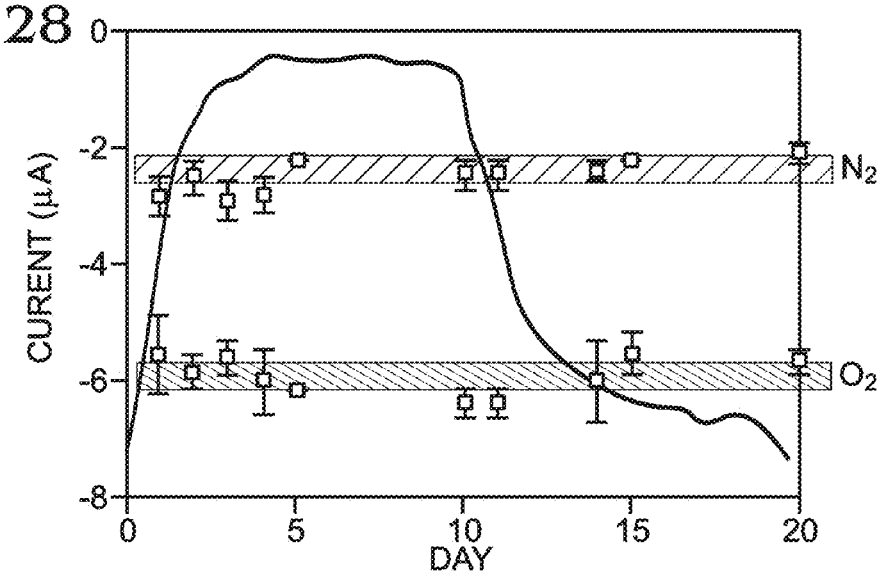
FIG. 28 is a graph showing current generation of an MCO catalyst immobilized to buckypaper via PBSE over a 20 day time period.
Figure 29:
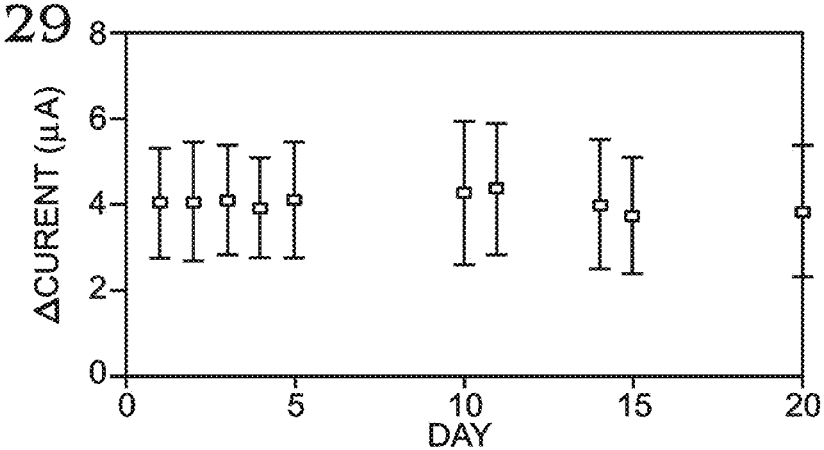
FIG. 29 is a graph showing current generation of an MCO catalyst immobilized to buckypaper via PBSE over a 20 minute time period.

Tafel plot is obtained by plotting the logarithm of measured current against the electrode potential as shown in FIGS. 24 and 25. The electron transfer rate constant is given by the following equation:

$$I_0 = nFAk_{et}$$

where $I_0$ is the current at which the two linear regions in the Tafel plot intersect, n is the number of electrons transferred, F is the Faraday's constant, A is the electrode surface area and ket is the electron transfer rate constant.

Example III

MCO Catalysts Immobilized to Buckypaper Via PBSE

Following on from previous success in stabilizing biological oxygen reduction catalysts by using a molecular tether [1-pyrenebutanoic acid, succinimidyl ester], we demonstrate continuous activity of a biocatalyst during its catalytic cycle for reduction of oxygen. Practical application of enzyme-based electrodes requires that the biocatalysts withstand environmental fluctuations, and produce reproducible power output, under continuous flow. Prior reports on stability of biological cathodes are often limited to storage, rather than sustained stability during catalytic cycling. Recent experimental investigations, however, use a laccase-functionalized conductive architecture that responds directly to dissolved oxygen and generates an amperometric output response. Biological cathodes fabricated in this way reduce oxygen at an onset potential of 0.635 V (vs Ag/AgCl), produce maximum current densities of ~100 μA/cm2 and exhibit sustained activity over a period of 20 days under continuous flow (5 ml/min). In addition, the stabilized electrode fabrication allows for stability during switching between nitrogen and oxygen saturated electrolyte. With an applied over-potential of 0.4 V, the current output of a laccase-functionalized electrode (via PBSE tethering) was stable and reproducible upon a repeated series of transitions from nitrogen to oxygen saturated electrolyte with no loss in the absolute change in current (~4 μA) over >1000 cycles and a period of 20 days.

FIGS. 26-29 show current generation from laccase-catalyzed oxygen reduction over time. As shown, the current output in response to changes in nitrogen or oxygen saturated electrolytes shows sustained activity over sequential electrolyte changes and over a period of 20 days.

Application to Alternative Catalysts: Cathodic Reactions

Figure 30:
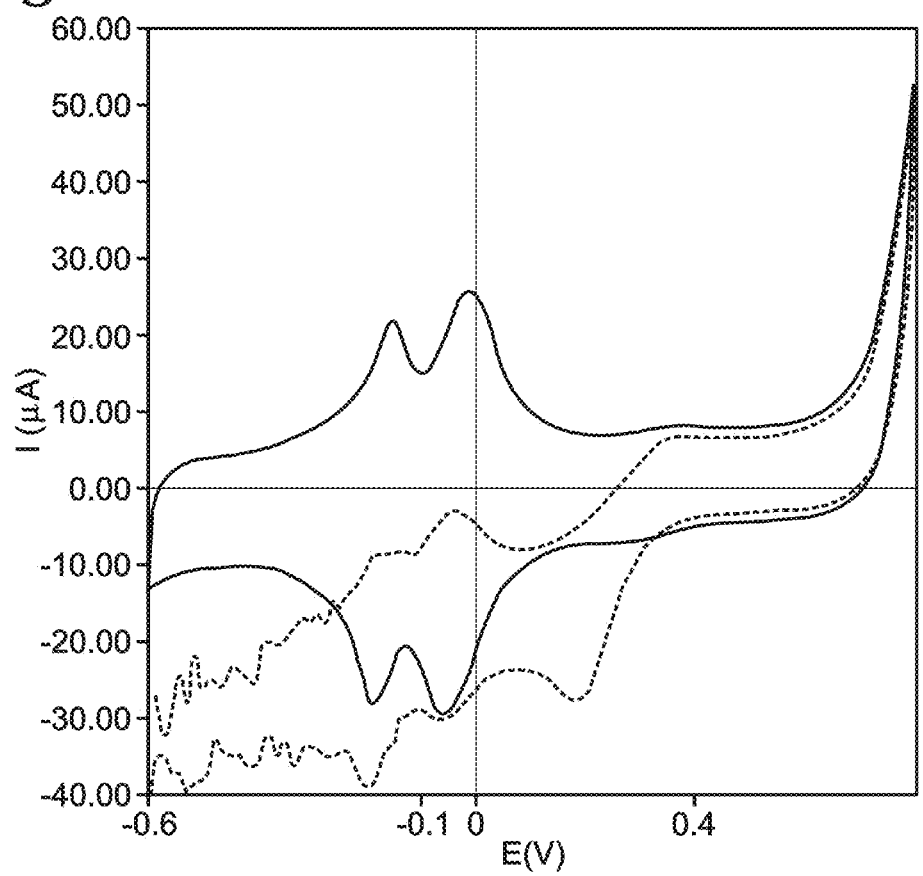
FIG. 30 is a cyclic voltammogram of sLAC immobilized to buckypaper electrodes via PBSE tethering.
Figure 31:
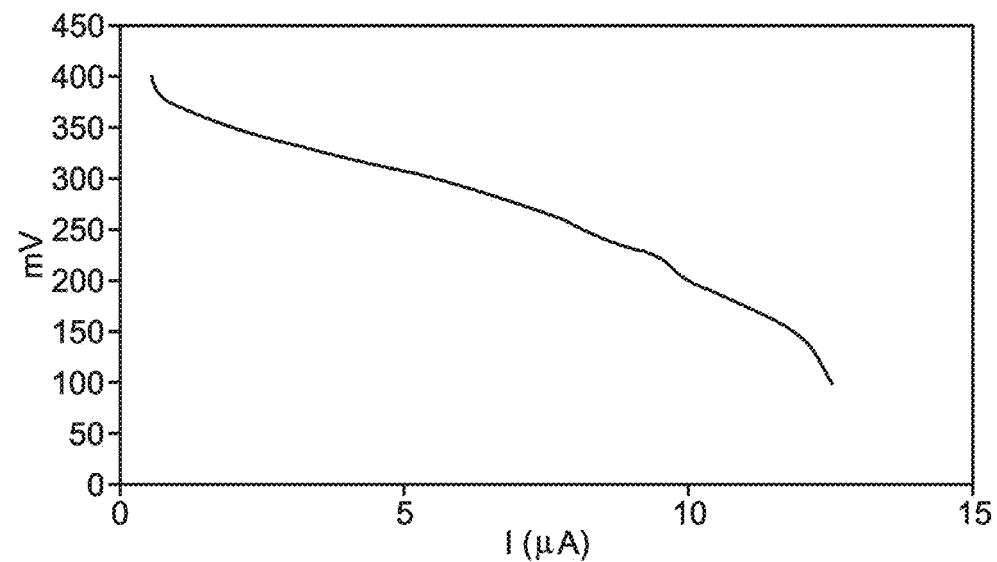
FIG. 31 is a polarization curve of sLAC immobilized to buckypaper electrodes via PBSE tethering.
Figure 32:
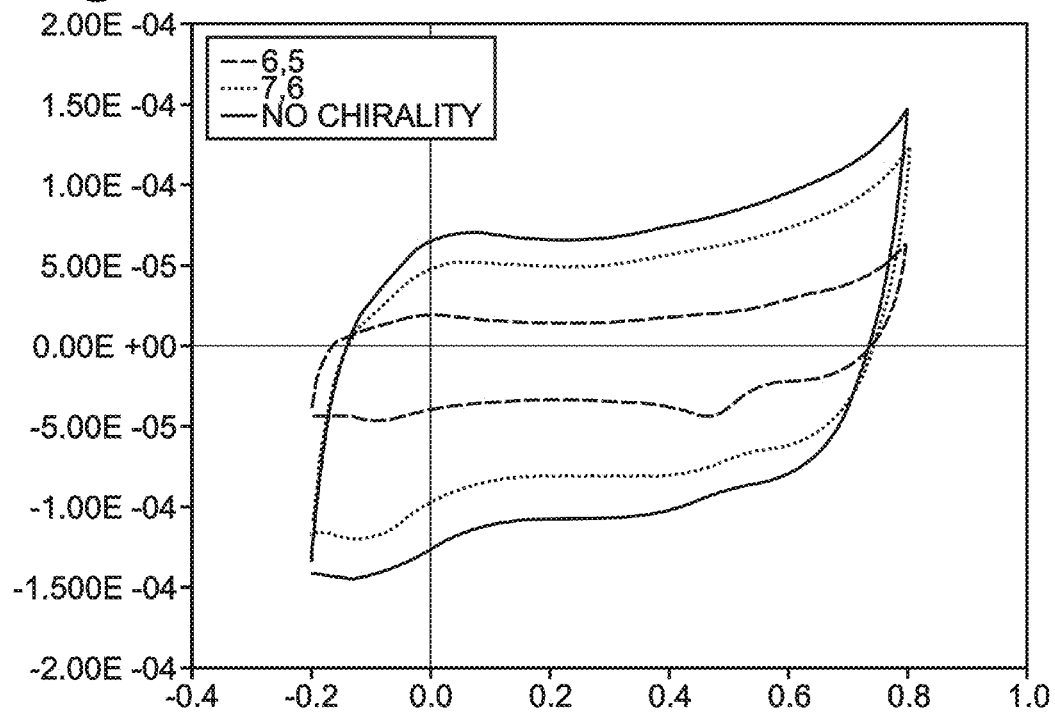
FIG. 32 is cyclic voltammogram of laccase immobilized with PBSE on single-walled carbon nanotubes of different chirality; no chirality SWCNTs, single-walled (6,5) chirality CNTs and single-walled (7,6) chirality CNTs.

Immobilization of a small laccase (sLAC) from Streptomyces coelicolor using PBSE tethering technology shows DET and evidence for oxygen reduction with an onset potential of approximately 400 mV (vs Ag/AgCl). FIGS. 30 and 31 show the cyclic voltammetry and polarization curve, respectively, of sLAC immobilized to buckypaper electrodes via PBSE tethering Effect of CNT Chirality on Adsorption of Enzyme Catalyst Carbon nanotubes may vary in their inherent chirality. Preliminary data following PBSE tethering of laccase suggests electrocatalytic activity of laccase that varies with carbon nanotube chirality (FIG. 32). The purity of current carbon nanotubes preparations limits the interpretation of this data to some extent, but specific interactions between the PBSE tether and carbon nanotubes of varying structural perturbations and defects may provide variations and potential optimization to electrode preparations.

Alternative Catalysts: Anodic Reactions

Figure 33:
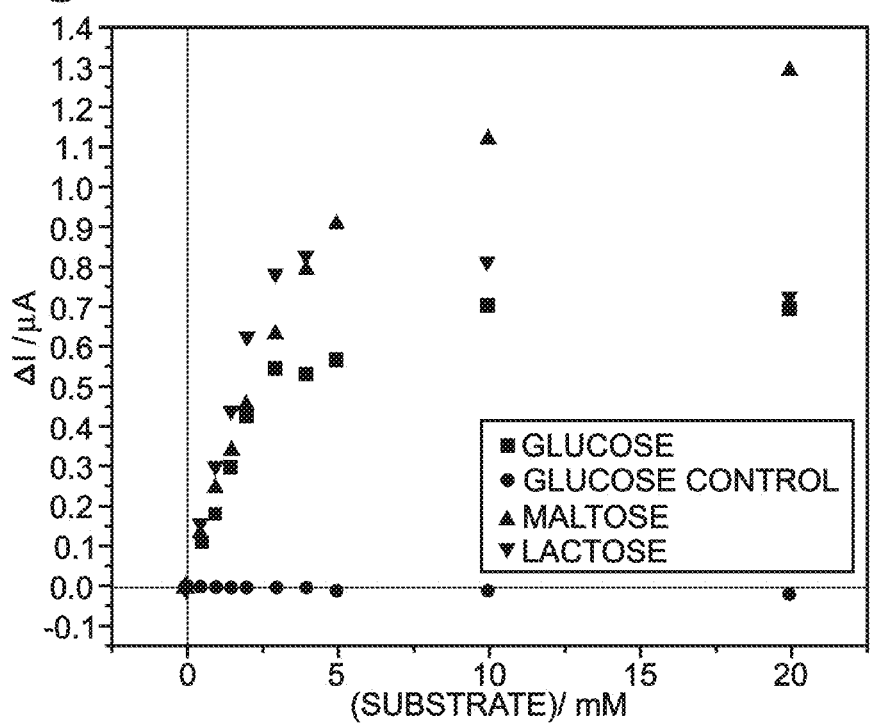
FIG. 33 is a graph showing specificity of PQQ_GDH immobilized to buckpaper via PBSE in response to various sugars.

Using the same "tethering" methodology described for laccase, the direct electron transfer of a PQQ-dependent glucose dehydrogenase (PQQ-GDH) was demonstrated with potential application to development of biological anodes. The utility of PQQ-GDH is in its remarkable substrate specificity for a wide range of sugars (FIG. 33). The enzyme demonstrates bio-electrocatalytic activity through direct electron transfer and experimental analysis revealed a concentration-dependent anodic current output in response to glucose, maltose, lactose and galactose. Anodes fabricated using PQQ-GDH demonstrated maximum current densities approaching 20 µA/cm2.

Example IV

Enzymatic Gas Diffusion Electrodes Incorporating Functionalized CNTs Fabrication of Gas-Diffusion Electrodes Chemistry—Molecular Tethering of CNT for Covalent Binding of Biocatalysts Carbon blacks (CB) and CNT were modified with different PTFE contents and used as base material for the biocatalytic layer. Various bi-functional crosslinkers were used to modify the CNT sidewalls with biocatalyst. In comparison to the non-conjugated crosslinker DSP, which nonspecifically binds to two primary amine groups, the tethered crosslinker PBSE and DDPSE have a defined aromatic functionality for specific π-π (stacking interaction with CNTs. The two additional protein binding "spacer arms" of DDPSE may provide more controlled and sterically fixed binding of an enzyme.

A size comparison of a 25 nm diameter MWCNT, 7 nm diameter laccase and 26 Å N-N distanced DDPSE is shown in FIG. 34. In this configuration, the MWCNT appears as an almost planar surface in respect to the crosslinkers and enzyme. The molecular structure of PBSE reveals a planar pyrene moiety of about 7 Å diameter whereas the DDPSE's heterocyclic region is significantly larger (~11 Å diameter) and with a slightly angled orientation that may provide a more spatially defined interaction that enhances the surface area for π-π-stacking interaction with the MWCNT surface. One may speculate that the perfectly planar PBSE should theoretically attach better than the angled orientation of DDPSE. Alternatively, however, DDPSE provides a larger surface area and more delocalized electrons for π-π-stacking interaction with the MWCNT surface. Additionally the presence of two succinimidyl moieties that act as "spacer arms" in DDPSE (rather than the single succinimidyl ester of PBSE) can bind to two amine groups of the same protein and thereby draw the protein closer to the MWCNT surface; 3 Å (C-N) in DDPSE versus 4 Å (C-N) in PBSE which favors a direct electron transfer from the laccase copper center to the carbon nanotube.

Materials—PTFE-Carbon Black and PTFE-MWCNT Composites

Figure 38:
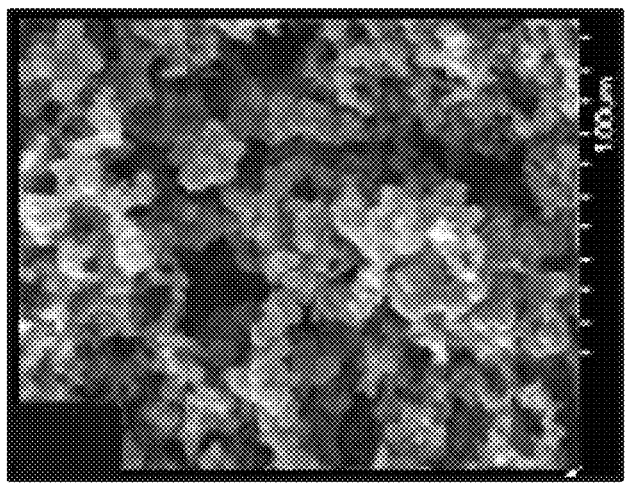
FIG. 38 is a higher magnification image of the PTFE-carbon black surface shown in FIG. 37 revealing a complete surface coverage with carbon black particles.
Figure 37:
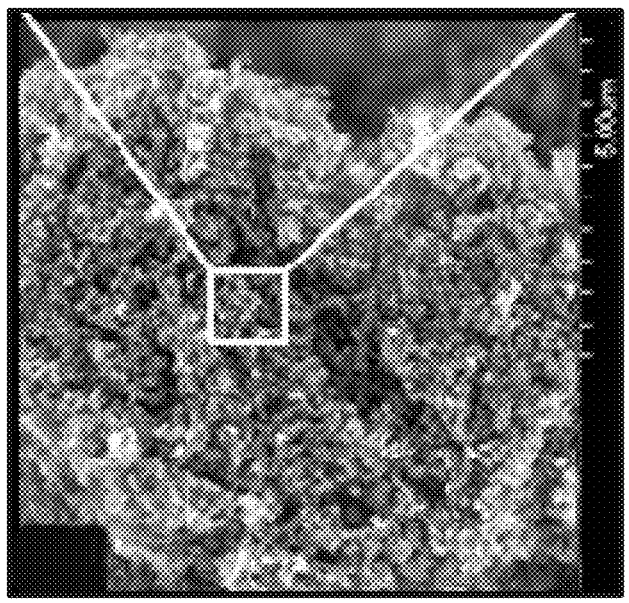
FIG. 37 is an SEM image of a PTFE modified carbon black micro emulsion droplet (35 wt % PTFE).
Figure 36:
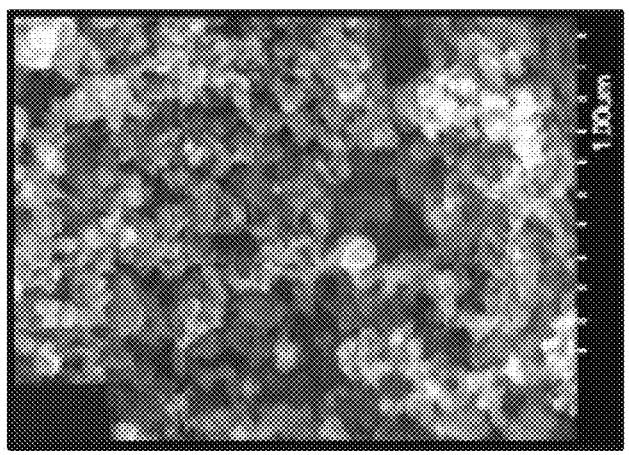
FIG. 36 is an SEM image of unmodified carbon black (Vulcan XC72R).

PFTE was selected as a binding material as a hydrophobic, but oxygen permeable polymer. In an aqueous process, carbon black particles (~5 nm diameter), are mixed with a suspension of PTFE particles (50 nm to 500 nm diameter; see FIG. 36). The highly hydrophobic PTFE forms micro droplets that are decorated on the outside with the more hydrophilic carbon black particles (FIGS. 37 and 38). The high magnification SEM images confirm the hierarchical structure of the resulting composite particles which are of spherical shape and several microns in diameter.

Figure 39:
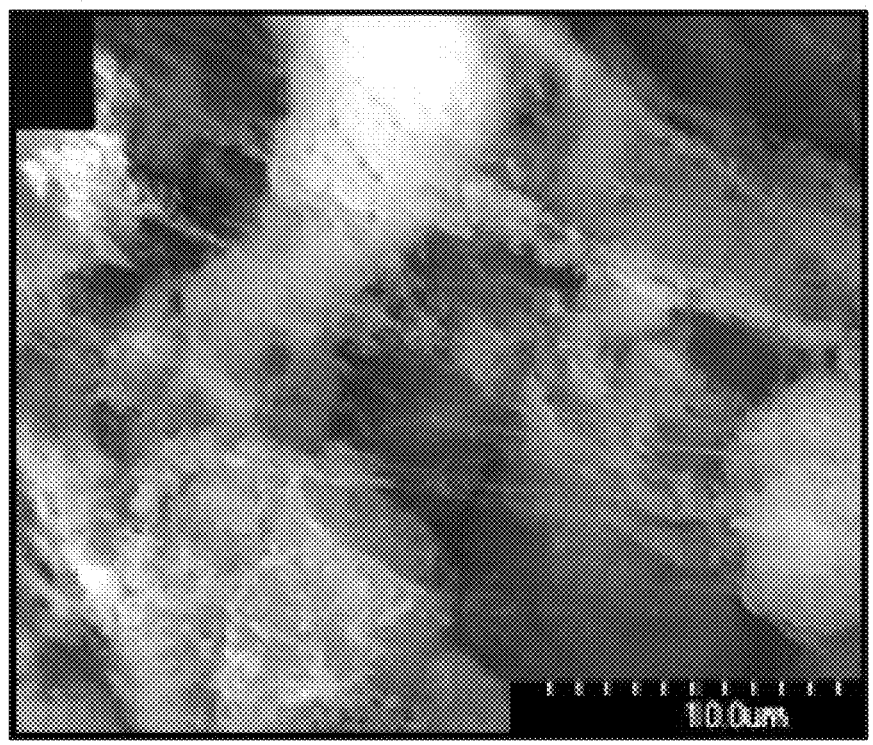
FIG. 39 is a high resolution SEM images of PTFE modified MWCNTs with 35 wt % PTFE.
Figure 40:
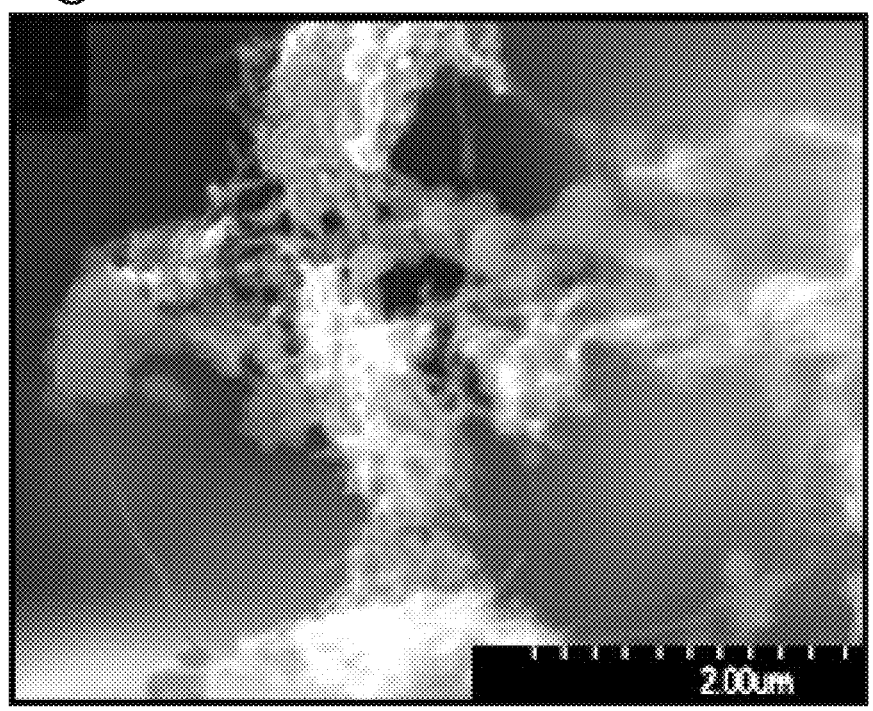
FIG. 40 is a high resolution SEM images of PTFE modified MWCNTs with 22 wt % PTFE.
Figure 41:
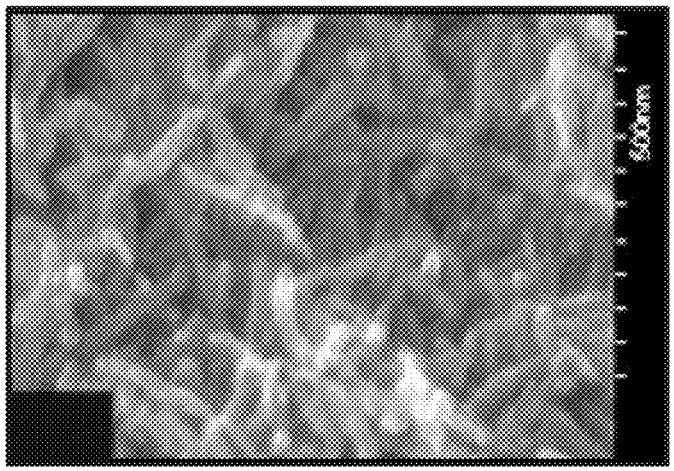
FIG. 41 is a high resolution SEM images of PTFE modified MWCNTs with 3.5 wt % PTFE.

Carbon nanotubes are known for their high electric conductivity, increased surface area and mechanical strength. Increased catalytic properties for MWCNT-carbon composites of a 50:50 ratio for ORR have been shown. See., e.g., Huang et al, incorporated by reference above. Creating a bi-layered gas-diffusion electrode with a carbon nanotube rich catalytic layer should theoretically increase the catalytic performance dramatically. As such, a derivative gas-diffusion electrode was prepared of a PTFE-CNT composite that could be directly pressed onto the carbon black gas-diffusion layer. FIGS. 39-41 show SEM images of the resulting MWCNT-PTFE composites of 35 wt %, 22 wt % and 3.5 wt % PTFE, respectively. The fiber like structure of the PFTE that binds the MWCNT together is noticeable in the resulting agglomerate. The amount of PTFE visibly decreases from FIGS. 39 to 41.

Figure 43:
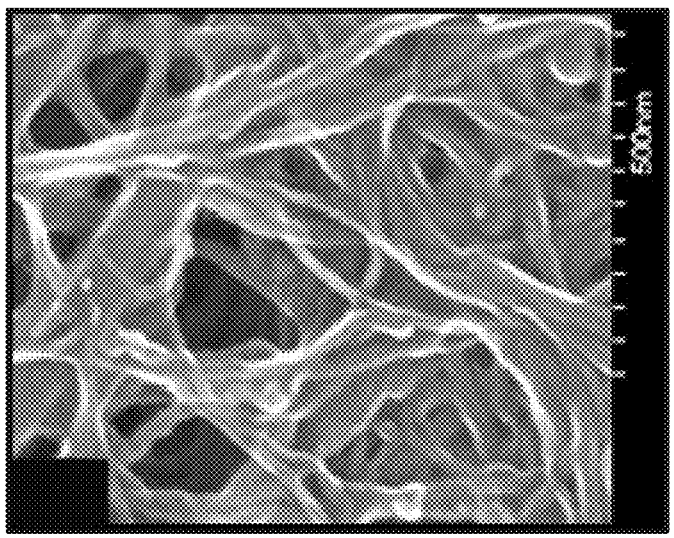
FIG. 43 shows MWCNT paper without binder after immobilization of laccase.
Figure 42:
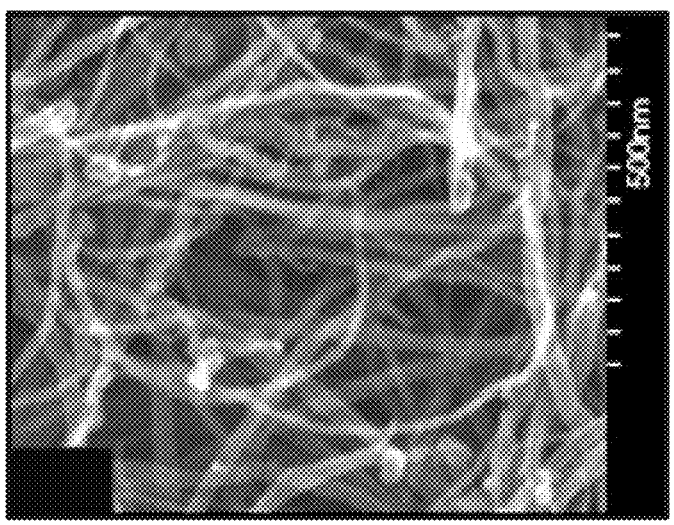
FIG. 42 shows MWCNT paper without binder before immobilization of laccase.

In order to maximize the electric conductivity of the MWCNT layer by eliminating any binding agents, a carbon nanotube paper (FIGS. 42 and 43) was introduced as a separate catalytic layer to which laccase could be readily immobilized. Accordingly, SEM imaging indicates a change in the morphology of the carbon nanotube paper that is attributed to the immobilization and distribution of laccase on the surface.

Characterization of Gas-Diffusion Electrode Air-Breathing Properties

To test the air-breathing properties of the gas-diffusion electrode, laccase was immobilized as an oxygen reducing biocatalyst directly onto the catalytic layer and the resulting open circuit potential monitored under oxygen, nitrogen and with ambient air. The air-breathing electrode is open to gases from the outside and to gas-saturated electrolyte from within. Under the influence of oxygen, the laccase-functionalized gas diffusion electrode shows a steady open circuit potential (OCP) of 0.53 V (vs. Ag/AgCl) which is close to the theoretical redox potential of the T1 copper center (FIG. 44). As expected, supplying nitrogen causes the OCP to drop to zero (i.e. the potential difference between carbon and the reference electrode). The slow decay over time (~1 hour) is attributed to small amounts of oxygen remaining in the electrolyte or carbon matrix. A comparable steady OCP of 0.536 V (vs. Ag/AgCl) is observed under oxygen, with only a minimal 2% decrease to 0.528 V upon switching to static ambient air (FIG. 45).

In general, the OCP reflects the difference in redox potential between the laccase, or its specific copper centers, in direct contact with the carbon electrode (versus the reference electrode and without any external load connected, or electric current flowing). OCP, therefore can be used as first evidence for an established direct electron transfer (DET) contact but cannot be used for specific quantification of enzyme or substrate concentration. Therefore OCP measured under the influence of oxygen, nitrogen and ambient air confirm effective air-breathing properties of our gas-diffusion electrode design with laccase as the oxygen reducing biocatalyst (FIGS. 44 and 45). The laccase-functionalized electrode is self-sustaining on oxygen supplied by ambient air alone and without any need of 'forced' gaseous convection.

Figure 46:
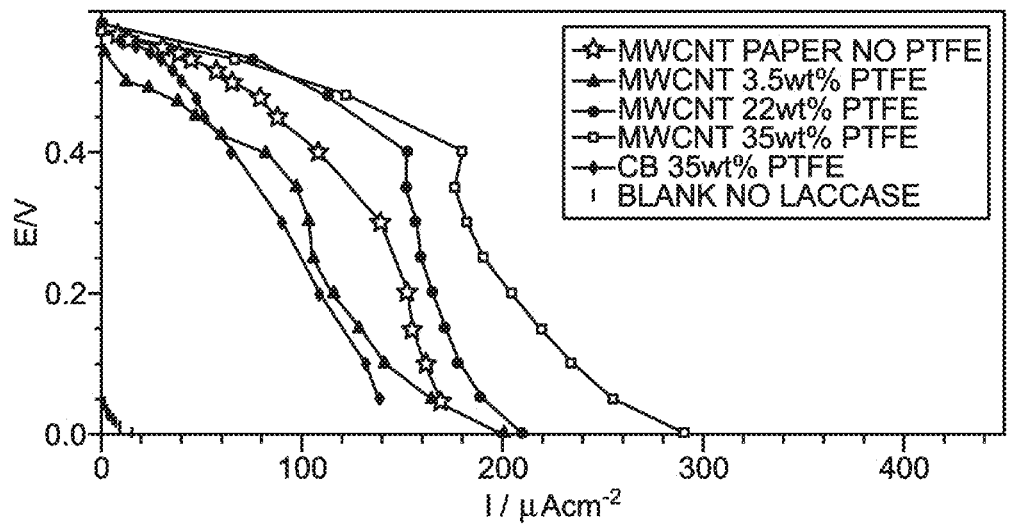
FIG. 46 is a potentiostatic polarization curves of enzymatic oxygen reduction on gas-diffusion electrodes (air breathing) with a carbon black/35 wt % PTFE gas diffusion layer and catalytic layers of different PTFE content (35 wt % to 0 wt % PTFE). Laccase was crosslinked with 20 mM DSP; 0.1 M PB, pH 6.3.
Figure 47:
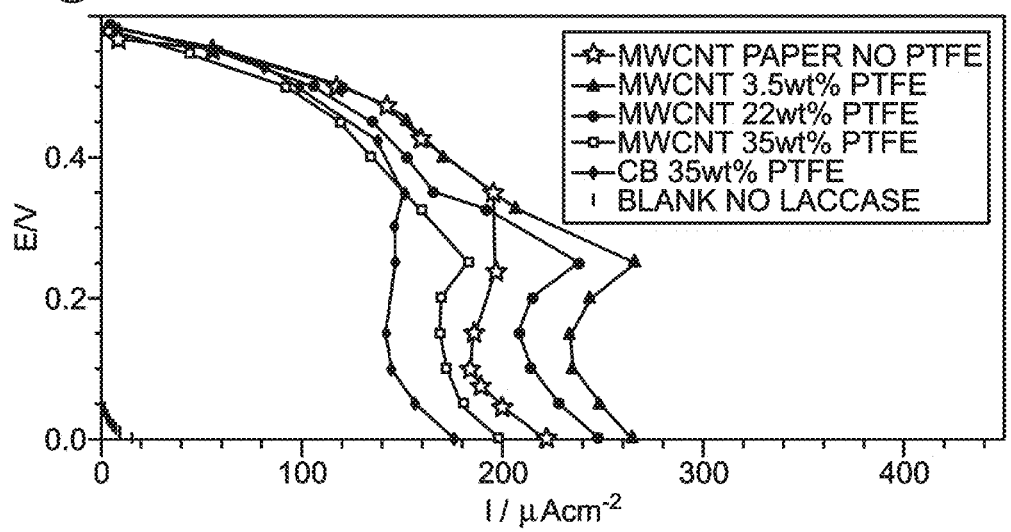
FIG. 47 is a potentiostatic polarization curves of enzymatic oxygen reduction on gas-diffusion electrodes (air breathing) with a carbon black/35 wt % PTFE gas diffusion layer and catalytic layers of different PTFE content (35 wt % to 0 wt % PTFE). Laccase was crosslinked with 20 mM PBSE; 0.1 M PB, pH 6.3.
Figure 48:
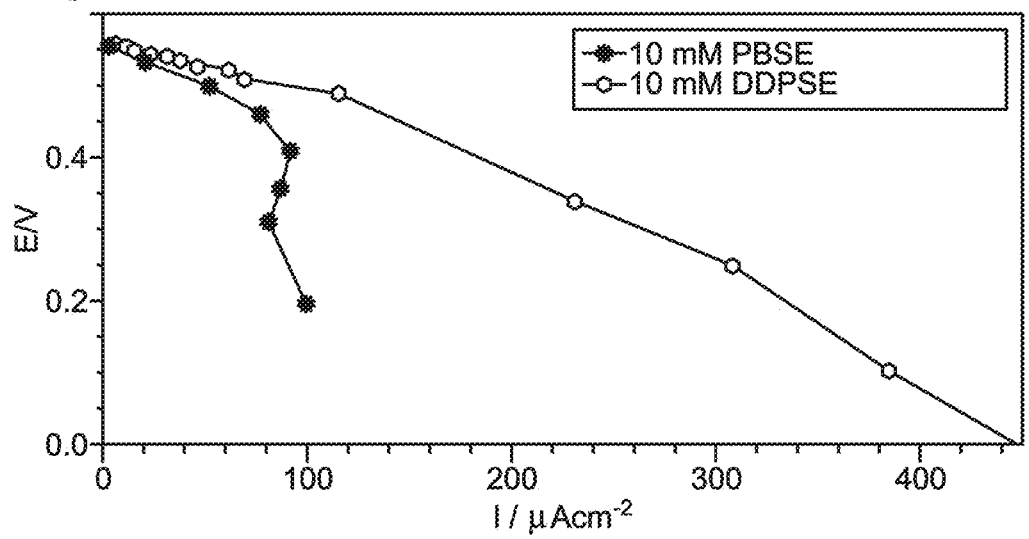
FIG. 48 is a potentiostatic polarization curves of enzymatic oxygen reduction on gas-diffusion electrodes (air breathing) with a carbon black/35 wt % PTFE gas diffusion layer and catalytic layers of different PTFE content (35 wt % to 0 wt % PTFE). Laccase was crosslinked with 10 mM DDPSE; 0.1 M PB, pH 6.3.

After characterizing the gas-diffusion layer for its air-breathing properties, we turned to defining the optimal hydrophilic-to-hydrophobic ratio of the carbon nanotube based catalytic layer. The polarization behavior of a range of gas-diffusion electrodes with MWCNT-PTFE layers, varying from 35-0 wt % of PTFE, was tested and compared to a pure carbon black/PTFE electrode (FIGS. 46-48). All polarization curves show almost no drop in potential (activation loss) after the first initial polarization, close to the OCP. The first segment (0.6 V to 0.45 V) of the polarization curves reveals a nearly linear dependence of the applied potential over the current density. This area, defined as 'the ohmic region', covers a fairly wide current range and represents the internal fuel cell resistivity loss. All three graphs in FIGS. 46-48 show an almost identical ohmic loss of about 0.1 V per 100 µA cm-1, regardless of the PTFE content and nature of crosslinking, indicating similar electrode and cell resistance. The higher current densities measured for the carbon nanotube modified electrodes in comparison to the pure carbon black cathodes are attributed to the higher surface area. Finally, in lower potential ranges between 0.45 V to 0 V, the mass transport regime becomes dominating. The kinetics of the catalytic reaction is determined by the limiting oxygen (fuel) supply probably caused by "flooded pores" inside the catalytic or gas-diffusion layer (as discussed above). In this area the efficiency of the biocatalyst in terms of oriented enzyme immobilization becomes important. It is in this region that changes in immobilization chemistry are predicted to define protein orientation and effectively influence catalysis. A comparison of three different crosslinkers demonstrates this effect. DSP, for example, adsorbs non-specifically to the carbon nanotube layer and covalently binds via two proteins amine groups. The tethered PBSE and DDPSE, in comparison, bind through stronger π-π stacking interaction directly at the CNT surface, leaving the succinimide ester groups for covalent attachment of enzymes. As shown in FIG. 46, the measured current densities for DSP crosslinked laccase decreases with increasing CNT content of the catalytic layer, indicating non-specific adsorption of enzyme agglomerates that show preferential binding to the more hydrophobic PTFE composites. In contrast, the current densities for the PBSE and DDPSE tethered laccase are higher for less teflonized composites with higher CNT ratios (FIGS. 47, 48). This observation further supports the idea of favored immobilization of biocatalysts by using a specific tethered crosslinker. As such, PBSE and DDPSE functionalized electrodes clearly shows an extension of the mass transport dominated regime compared to DSP (non-specific adsorption) controls (FIGS. 46, 47), as the multi-walled catalytic layer provides a higher surface area and favors the attachment of tethered crosslinker. The lower the PTFE content the more MWCNT surface area is accessible for enzyme, and as a result, the current densities achieved are almost double with MWCNTs (3.5 wt % PTFE) compared to carbon black. To further confirm the concept of improved interaction of CNTs and tethered crosslinker we compared PBSE with DDPSE, which has a much larger area for interaction and for π-π-stacking. For identical linker concentrations a significant increase in current density was observed on MWCNT paper modified with DDPSE, where current densities at 0.3 V were 3-fold higher for DDPSE over PBSE (FIG. 48). The advantages of DDPSE over PBSE are clear: (i) it establishes stronger π-π-interactions with the MWCNT surface, (ii) it can covalently bind to two amine groups of the same enzyme and position the protein it in a more defined orientation and (iii) the electron transfer distance is significantly reduced; about 1 Å shorter).

Figure 49:
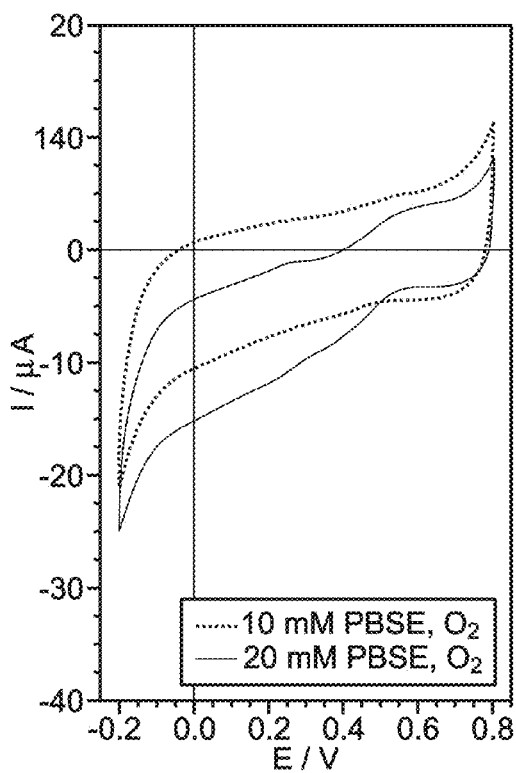
FIG. 49 is a cyclic voltammograms for laccase catalyzed oxygen reduction. Laccase was immobilized on MWCNT paper using PBSE; 0.1 M PB, pH 6.3, 10 mV s-1.
Figure 50:
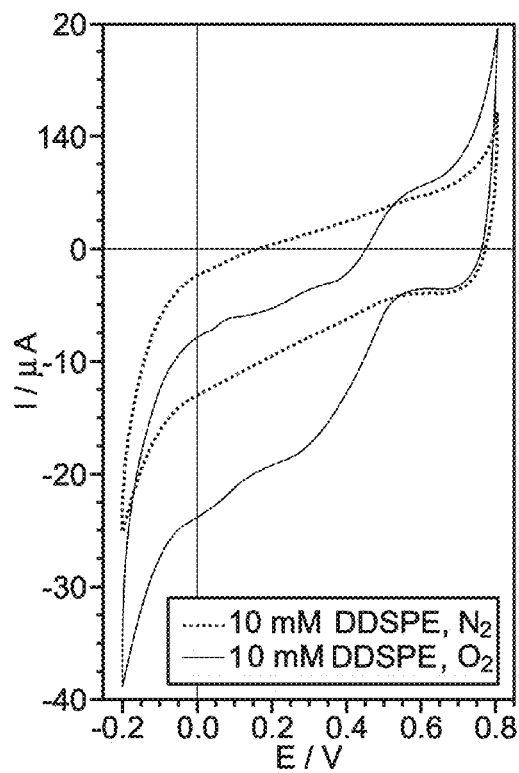
FIG. 50 is a cyclic voltammograms for laccase catalyzed oxygen reduction. Laccase was immobilized on MWCNT paper using DDPSE, 0.1 M PB, pH 6.3, 10 mV s-1.

To further support the preferential efficiency of DDPSE-functionalized carbon nanotubes for enzyme modification, cyclic voltammograms (CV) measurements were investigated for laccase tethered to MWCNT paper via alternative crosslinkers. Identical concentrations of crosslinker were selected and for control experiments, the ORR activity was tested in aerobic and anaerobic conditions. The CVs in FIGS. 49 and 50 show a dramatic increase in oxygen reduction current by using DDPSE as crosslinker. The onset potential for the enzymatic ORR is about 0.55 V (vs Ag/AgCl) which agrees with the reported OCPs. The CV in nitrogen purged solution shows no catalytic current, confirming the direct electrical communication between laccase and electrode.

CONCLUSIONS

Carbon black-PTFE based gas-diffusion electrodes provide a paradigm for efficient oxygen supply for multicopper oxidase catalyzed ORR reactions. The introduction of MWCNT-PTFE composite materials, however, readily provides a method to manufacture catalytic layers for gas-diffusion electrodes of variable shapes and sizes. The modification with carbon nanotubes provides a higher surface area for enzyme immobilization and a better conductivity that results in reduced ohmic losses under polarization condition. Further, a MWCNT surface modification with tethered crosslinker, such as PBSE or DDPSE, clearly increases the DET efficiency between biocatalyst and carbon nanotube. The π-π-stacking interaction provides a stronger binding between MWCNT and protein that through simple physisorption alone. Preliminary data also suggests that DDPSE's two covalent spacer arms covalently bind and position the enzyme closer the electrode surface and reduce the electron transfer distance.

Teflonization of Carbon Blacks and MWCNT:

4.5 g of a 60 wt % PTFE dispersion (Dupont) in 150 mL DI water were slowly added to a suspension of 5 g of carbon black (Vulcan©72R, Cabot Corp., MA, USA) in 300 mL 60° C. DI water under stifling. The hot mixture was stirred for 30 minutes and allowed to cool for about 2 hours, during which time a precipitate forms. The filtrate was carefully washed with DI water, dried at 90° C. over night and then heated to 150° C. for 30 minutes before slowly cooling to room temperature. A final grinding process results in a fine black powder without any visible PTFE residues. The MWCNT-PTFE (MWCNT: 20-30 nm diameter, 10-30 um length, cheaptubes.com, VT, USA) composites were prepared at a range of concentrations, following the described protocol in a 1% IPA-water solution to achieve a better carbon nanotube distribution than water alone; 4.5 g, 2.8 g and 0.45 g of 60 wt % PTFE dispersion were added to achieve composites with 35 wt %, 22 wt % and 3.5 wt % PFTE, respectively.

Preparation of Gas-Diffusion Electrode:

About 80 mg of the carbon black PTFE composite (35 wt % PTFE) were placed into a round shaped die (0.75 inch diameter) and hand-pressed onto a nickel mesh to form the gas-diffusion layer. About 40 mg carbon or MWCNT PTFE composite were placed on top of the gas diffusion layer to form the catalytic layer. Both layers were pressed together for about 5 minutes at a pressure of 1 klbs. For the binder free MWCNT layer, a circle (0.5 inch diam.) of MWCNT paper (Buckeye Composites, OH, USA) was placed on top of the gas-diffusion layer and pressed together as before.

Immobilization of Enzymes:

The crosslinkers DSP (Dithiobis(succinimidyl propionate)), PBSE (1-Pyrenebutyric acid N-hydroxysuccinimide ester) and DDPSE (4,4'-[(8,16-Dihydro-8,16-dioxodibenzo[a,j]perylene-2,10-diyl)dioxy]dibutyric acid di(N-succinimidyl ester)) were purchased from Sigma (St. Louis, Mo., USA). The catalytic side of the gas-diffusion electrodes were exposed to 0.5 mL of a 20 mM crosslinker solution in DMSO for about 2 hours. The activated electrodes were rinsed with DMSO and DI water and incubated at 4° C. over night with 0.5 mL of 8 mg mL-1 laccase in 0.1 M phosphate buffer (PB), pH 6.3.

Electrochemical Measurements:

Electrochemical measurements were performed in a stackable 3-electrode cell as reported earlier[38] with a Pt-counter and a Ag/AgCl (3 M KCl) reference electrode. The stack cell has an inner diameter of 0.5 inch. The air-breathing gas-diffusion electrodes are placed on the bottom of the stack cell with the gas-diffusion layer exposed to the ambient air and the catalytic layer in contact with the internal electrolyte. All measurements were performed in 0.1 M phosphate buffer, pH 6.3.

What is claimed is:

1. A catalytic electrode formed by:
   (a) attaching a carbon nanotube to the surface of an electrode;
   (b) attaching the linking agent, DDPSE, to the sidewall of the nanotube via a π-π interaction; and
   (c) attaching a catalytic enzyme to the DDPSE, wherein the catalytic enzyme is either a multicopper oxidase (MCO) or PQQ-dependent glucose dehydrogenase
   wherein DDPSE is 4,4'-[(8,16-Dihydro-8,16-dioxodibenzo[a,j]perylene-2,10-diyl)dioxy]dibutyric acid di(N-succinimidyl ester).

2. The electrode of claim 1 wherein the catalytic enzyme is a MCO.

3. The electrode of claim 2 wherein the MCO is laccase.

4. The electrode of claim 2 wherein the MCO is bilirubin oxidase.

5. The electrode of claim 1 wherein the catalytic enzyme is PQQ-dependent glucose dehydrogenase.

* * * * *